United States Patent [19]

Matsumura et al.

[11] 4,213,056

[45] Jul. 15, 1980

[54] METHOD AND APPARATUS FOR DETERMINING THE STATE OF INTERLACING IN INTERLACED MULTIFILAMENT YARNS

[75] Inventors: Seiji Matsumura; Nobuo Kusumoto, both of Matsuyama, Japan

[73] Assignee: Teijin Limited, Osaka, Japan

[21] Appl. No.: 940,482

[22] Filed: Sep. 7, 1978

[30] Foreign Application Priority Data

Sep. 12, 1977 [JP] Japan .................................. 108901
Sep. 12, 1977 [JP] Japan .................................. 108902

[51] Int. Cl.² .......................................... G01N 21/30
[52] U.S. Cl. ................................. 250/559; 73/160; 356/238
[58] Field of Search ............ 250/559, 562, 571, 572; 73/160, 159; 356/238

[56] References Cited

U.S. PATENT DOCUMENTS 3,793,883 2/1974 Goldfarb et al. .................... 73/160
4,103,177 7/1978 Sanford et al. ...................... 356/238

Primary Examiner—David C. Nelms
Attorney, Agent, or Firm—Burgess, Ryan and Wayne

[57] ABSTRACT

Disclosed is a method and apparatus for determining the state of interlacing in interlaced multifilament yarn, wherein an interlaced multifilament yarn is forced to contact a contact member while running along a yarn passage so that a configuration of the yarn is changed with regard to the mutual lateral positions of individual filaments thereof. The state of the above-mentioned changing of the yarn configuration is detected by means of a photoelectric principle, and the degree of interlacing is electrically calculated from the detected signal.

24 Claims, 35 Drawing Figures

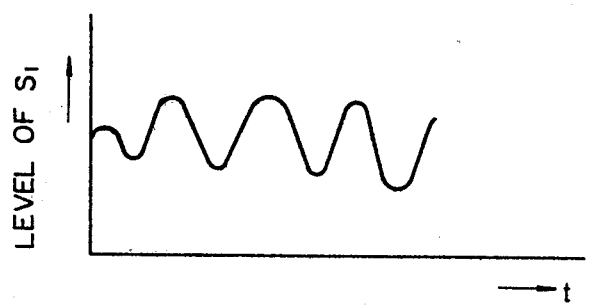
Fig. 3A
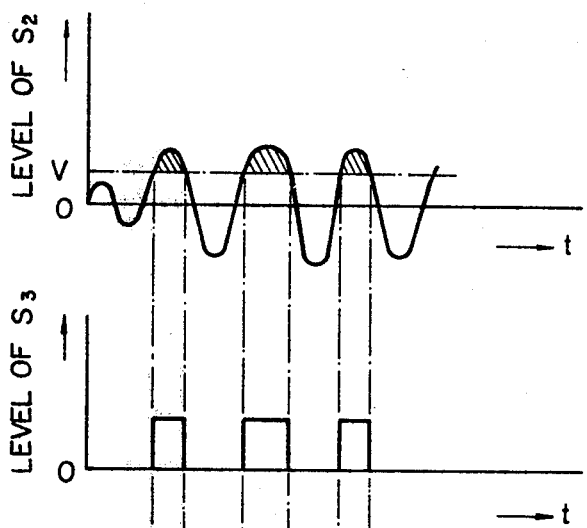
Fig. 3B
Fig. 3C
Fig. 3D

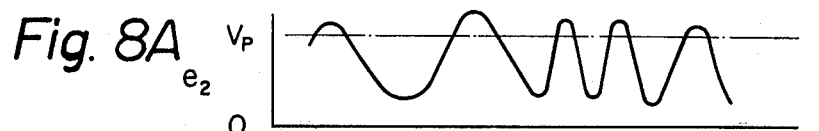
Fig. 8A $e_2$
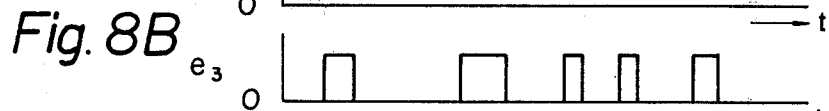
Fig. 8B $e_3$
Fig. 8C $e_4$
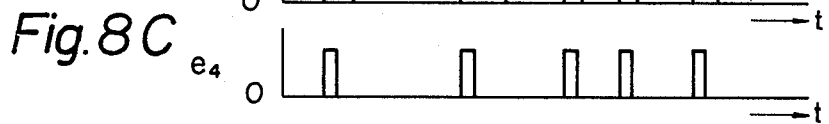
Fig. 8D $e_5$
Fig. 8E $e_6$
Fig. 8F $e_7$
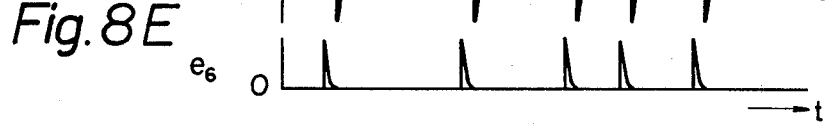
Fig. 8G $e_8$
Fig. 8H $A_H$
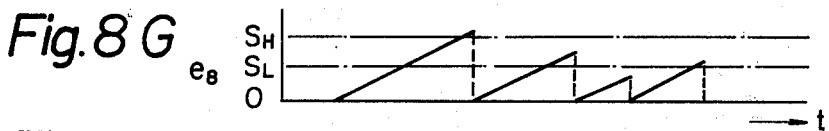
Fig. 8I $A_L$

METHOD AND APPARATUS FOR DETERMINING THE STATE OF INTERLACING IN INTERLACED MULTIFILAMENT YARNS

BACKGROUND OF THE INVENTION (1) Field of the Invention

The present invention relates to a method and apparatus for determining the degree of interlacing of individual filaments in interlaced multifilament yarns.

In the instant specification and claims, by the term "interlaced multifilament yarn" is meant not only an interlaced multifilament yarn which has been processed by an interlacing machine and formed into a yarn package, but also an interlaced multifilament yarn which has been processed by an interlacing machine and is running toward a yarn package forming device for forming it into a yarn package. The term "interlaced multifilament yarn" is used in a very wide sense so that the conventional interlaced multifilament yarn made from such material as polyester, polyamide, acetate multifilament yarn, etc., is covered.

(2) Description of the Prior Art

The degree of interlacing, which is expressed by the number of entanglements along the unit length of yarn, or the coherency factor, which is expressed by the average yarn length between two entanglements, is an important factor for defining the quality of interlaced multifilament yarns. As the method for determining such characteristics, there has been adopted the hook-drop test method. According to this method, a contact probe is inserted into the yarn, by moving the contact probe or yarn, the entanglement is detected by the force or displacement the probe undergoes on passage through the entangled portion and characteristics such as the degree of interlacing are thus determined. An apparatus for performing this hook-drop test automatically is disclosed in the specification of U.S. Pat. No. 3,290,932.

As will be apparent from the above-mentioned measurement principle, in order to detect entanglements assuredly according to the hook-drop test method, it is necessary to move the yarn or contact probe at a low speed. Therefore, this method involves a defect that the measurement efficiency is very low. For example, the measurement is ordinarily conducted at a running speed lower than 5 m/min, and more than 1 minute is necessary for completing the measurement on a yarn sample having a length of 5 to 10 m.

As pointed out above, the degree of interlacing is a very important factor for evaluating the quality of interlaced yarns. Accordingly, at the inspection step in the interlaced yarn manufacturing process, a great number of sample packages should be picked up from products and tested for quality control. Since the number of samples to be tested is very large and the measurement operation now adopted is very troublesome, there is brought about a disadvantage that the measurement is labor-consuming. Further, at the inspection step, only a very minute portion of a sampled product package is tested. Accordingly, a temporary and abnormal change of the interlacing degree during production cannot be detected. This is another defect of the conventional test method.

BRIEF SUMMARY OF THE INVENTION

It is, therefore, a primary object of the present invention to provide a method and apparatus for determining the state of interlacing in interlaced multifilament yarns, in which the state of interlacing can be determined at a high speed with a high reliability while eliminating the foregoing defects and disadvantages involved in the conventional method and apparatus.

Another object of the present invention is to provide a method and apparatus for determining the state of interlacing in interlaced multifilament yarns, which can be applied to the interlaced multifilament yarn manufacturing process for the purposes of quality control and process inspection.

In accordance with a fundamental aspect of the present invention, the above mentioned objects can be attained by a method comprising causing an interlaced multifilament yarn to run while being in contact with a contact member under a predetermined contact pressure, thereby to produce changes in the configuration of the yarn, and determining the state of interlacing by measuring the changes in the configuration. This method is characterized in that the state of interlacing is determined by utilizing the following phenomenon caused when an interlaced multifilament yarn is caused to run while being in contact with a contact member under a predetermined contact pressure. Namely, when the interlaced yarn is caused to run in such a manner, in the region of contact with the contact member the respective individual filaments of the interlaced multifilament yarns are spread in a direction at a right angle to the running direction, i.e., in the lateral direction, according to the state of interlacing or entanglement among the respective individual filaments.

In the method of the present invention, in order to determine the degree of interlacing in interlaced multifilament yarns promptly and with a high reliability, the length of the yarn which runs during a time for measuring the state of interlacing is simultaneously measured, and the degree of interlacing is calculated by conducting an operation based on both the measured value representing the change of the configuration and the measured value of the yarn length.

It is generally known that a draw-textured yarn has the problem of tight spots wherein multifilaments which compose the draw-textured yarn and which are not detwisted gather together. Tight spots can easily be detwisted when the draw-textured yarn is tensioned with a detwisting tension equal to or more than 0.2 g. per denier, which detwisting tension can be much lower than the tension necessary to release the entanglement from interlaced portions.

From the standpoint of controlling the quality of a draw-textured and interlaced yarn, it is necessary to distinguish tight spots from interlaced portions. When the methods according to the present invention are applied to a draw-textured and interlaced yarn under the conditions of two different tensions, the tight spots in the draw-textured and interlaced yarn can be easily distinguished from the interlaced portions. More specifically, in the first measurement the total number of tight spots and interlaced portions is measured under the first tension which does not detwist the tight spots and which does not release the entanglement from the interlaced portions in the yarn, and then the number of the interlaced portions is measured under the second tension which can detwist the tight spots but which does not release the entanglement from the interlaced portions. As a result, the number of interlaced portions can be obtained from the measurement under the second tension and the number of tight spots can be obtained as a difference between the data obtained from the measurements under the first and the second tensions. When the methods according to the present invention are applied to the same single draw-textured and interlaced yarn by varying the tension level, effective information regarding the quality control of the draw-textured and interlaced yarn, such as the respective numbers of tight spots and interlaced portions, can be obtained.

That is the above-mentioned method for determining the state of interlacing in interlaced multifilament yarns is directly applied to the step of taking out processed yarns in the interlaced multifilament yarn manufacturing process and the determined value representing the state of interlacing is adopted as a measure indicating the degree of interlacing in the interlaced yarns for the purposes of quality control and process inspection.

To carry out the above-mentioned method according to the present invention, there is provided an apparatus for practising the above-mentioned methods, which comprises a contact body disposed in a yarn passage for an interlaced multifilament yarn, at least a portion of the contact body in contact with the interlaced multifilament yarn being light-transmitting, tensioner means for imparting a contact pressure to the yarn so that a predetermined contact pressure is applied to the running yarn while it is in contact with the contact body, a light source and a photoelectric conversion element disposed with the contact body being interposed therebetween so that the light axis intersects the contact portion of the contact body, electric means for selectively extracting a time series alternating current component alone from a signal of the photoelectric conversion element and converting it to a corresponding time series pulse signal, and another electric means for processing the pulse signal and transmitting a signal indicating the state of interlacing in the interlaced multifilament yarn.

In order to determine the degree of interlacing of interlaced multifilament yarns promptly and with a high reliability in the above-mentioned fundamental apparatus, means for measuring the length of the running yarn while it is in contact with the contact body and computer means for automatically calculating the degree of interlacing which indicates the interlacing state from the signal issued from the electric means and a measurement length of yarn are further attached to the above-mentioned fundamental apparatus.

For the purpose of applying the above-mentioned fundamental apparatus to quality control and process inspection in the interlaced yarn manufacturing process, there is adopted a system in which the electric means for transmitting a signal indicating the state of interlacing in the interlaced yarn is an electric means for generating a time series of electric signals, each having an intensity corresponding to the time interval between two adjacent points of generation of generating pulses in the pulse signal of the time series issued from the pulse signal-emitting electric means; and an electric discriminating means is disposed to produce a particular electric signal when the intensity of the electric signal from the means for generating a time series of electric signals is above or below the upper or lower predetermined limit. In this system, the above-mentioned contact body is disposed along a yarn passage at a position between the means for interlacing the supplied multifilament yarn and a take-up means, and an alarm device is disposed in the interlacing machine in such a manner that it is actuated by the signal from the electric discriminating means, to perform the process inspection.

Still further, for the purpose of integrated control in the interlaced yarn manufacturing process, there is disposed central inspecting display means showing outputs of computing means of measurement devices mounted on the respective spindles of the interlacing machine.

BRIEF EXPLANATION OF THE DRAWINGS

FIG. 3A is a waveform of a sequential electric signal issued from the light receiving device of the unit illustrated in FIGS. 2A and 2B, FIGS. 3B, 3C and 3D are waveforms of sequential converted electric signals corresponding to the diagram illustrated in FIG. 3A.

DETAILED DESCRIPTION OF THE PREFERRED EMBODIMENTS

Figure 1A:
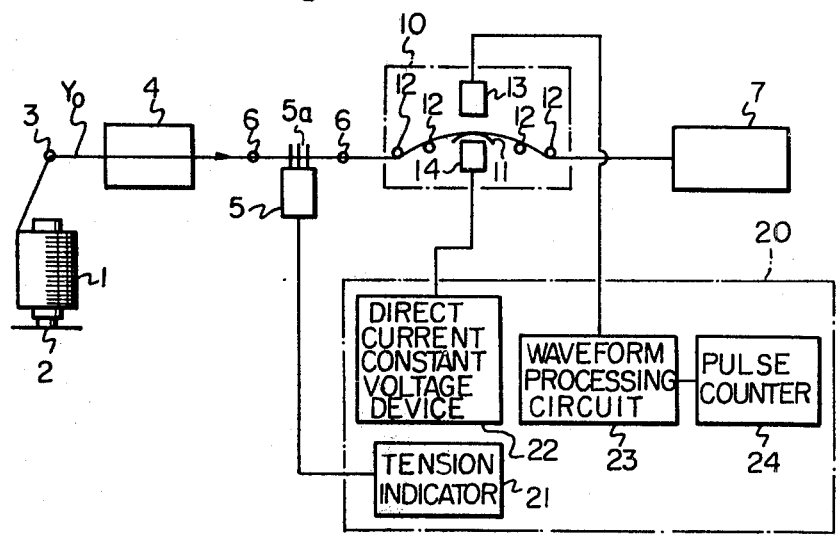
FIG. 1A is a schematic drawing indicating the essential elements of the measuring apparatus according to the present invention.

For the sake of imparting a clear understanding the present invention, the basic technical concept of the present invention will first be described.

When a running interlaced multifilament yarn (hereinafter referred to simply as "yarn") is pressed onto a yarn contact body in a direction intersecting the yarn running direction at a right angle, the configuration of the yarn is changed so that individual filaments constituting the yarn are dispersed along the contact member. It has been found that this change of the configuration is not uniform. From the results of various experimental tests, it was confirmed that this change of the configuration depends on the degree of interlacing of the yarn. The reasons for this are considered to be as follows.

When a multifilament yarn consisting of a number of individual filaments is brought into contact with the above-mentioned contact body under the application of a contact pressure, if there is no force restricting the movement of the individual filaments in a direction at a right angle to the running direction of the yarn, namely in the lateral direction, the individual filaments are relatively displaced in the lateral direction along the yarn contact surface of the contact body by the contacting pressure under yarn tension and such change of the configuration is caused in the yarn so that the entire yarn is flattened, namely expanded in the lateral direction. Since individual filaments of the yarn are entangled and interlaced with one another, it is considered that a force restricting the movement of the individual filaments of the yarn in the lateral direction is generated owing to such entanglements among the individual filaments and that this restricting force is proportional to the degree of interlacing. Therefore, the above-mentioned change of the configuration takes place depending on the relation between the above-mentioned pressing force and restricting force. Accordingly, if the pressing force is kept constant, creation of the change of the configuration depends only on the force which restricts the lateral movement of the individual filaments of the yarn. Namely, hardly any change of the configuration takes place in an area where the degree of interlacing of the individual filaments is high and the above-mentioned restricting force is large, namely in an interlaced portion; but the change of the configuration is conspicuous in an area where the degree of interlacing of the individual filaments is low and the above-mentioned restricting force is small, namely in a noninterlaced portion. Therefore, it is considered that the presence and state of the interlaced portion in the yarn can be detected based on this change of the configuration. This has been confirmed by results of experiments conducted by using the apparatus of the present invention and a conventional apparatus, which will be described hereinafter.

The fundamental apparatus according to the present invention will now be described with reference to the accompanying drawings.

Figure 1B:
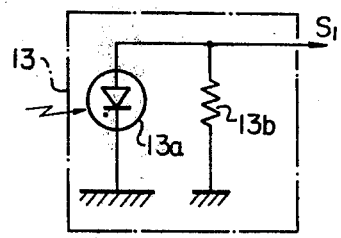
FIG. 1B is a schematic diagram indicating the electric circuit of a light receiving device utilized for the measuring apparatus illustrated in FIG. 1A.
Figure 1C:
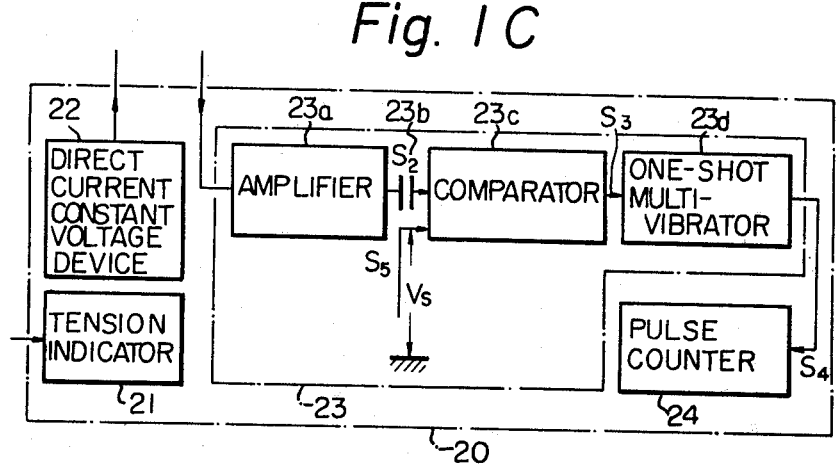
FIG. 1C is a block diagram indicating the waveform processing circuit and related electric circuit utilized for the apparatus illustrated in FIG. 1A.

Referring to FIGS. 1A, 1B and 1C, a yarn $Y_O$ to be tested is taken up at a predetermined speed from a yarn package 1 mounted on a bobbin holder 2 to a conventional take-up device 7 through a yarn guide 3, a tension control device 4, a conventional tension detector 5 provided with a feeler 5a and an interlaced portion detecting zone 10. A predetermined tension is applied to the yarn $Y_O$ by the tension control device 4. A known tension roller system or the like can be used as the tension control device 4. The tension is detected by the detector 5 and the signal issued from the detector 5 is input to a tension indicator 21 mounted on a body portion 20 of a measurement apparatus. Yarn guides 6 are disposed before and after the tension detector 5 to form a predetermined yarn passage and ensure stable measurement of the tension.

Figure 2A:
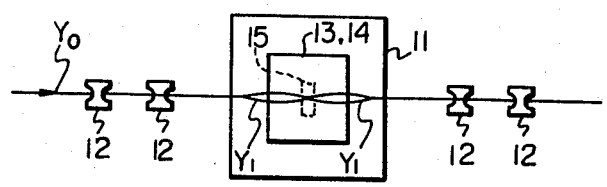
FIG. 2A is a schematic drawing of a unit for detecting the state of configuration of the running yarn, which is utilized for the apparatus illustrated in FIG. 1A.
Figure 2B:
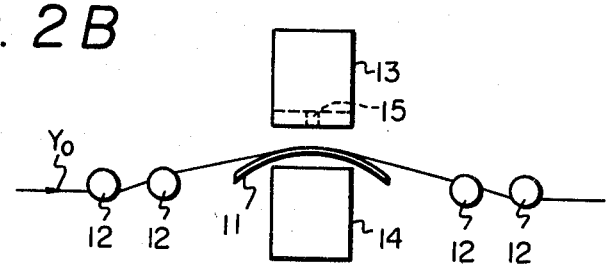
FIG. 2B is a schematic side view of the light source and the light receiving device, utilized for the unit illustrated in FIG. 2A.

As illustrated in detail in FIGS. 1A, 2A and 2B, the interlaced portion detecting zone 10 comprises a contact body 11 having an arcuate section and being composed of a light-transmitting substance such as glass, four guides 12 for guiding the yarn along a predetermined yarn passage to the contact body 11, and a light source 14 and a light receiving device 13 located at a position corresponding to the position of the yarn contact portion of the contact body 11, with the contact body 11 being interposed therebetween. Referring to FIG. 1A, electric power is supplied to the light source 14 from a direct current constant voltage device 22 mounted in the body portion 20 of the measurement apparatus, and the output signal produced from the light receiving device 13 is applied to a waveform processing circuit 23 arranged in the body portion 20 of the measurement apparatus to process the waveform of the output signal for waveform shaping. The output signal from the waveform processing circuit 23 is applied to a pulse counter 24.

The method for determining the state of interlacing according to the present invention will now be described by reference to the embodiment having the above-mentioned structure.

As shown in FIG. 2A, the yarn $Y_O$ to be tested is caused to run while being guided by the guides 12 so that it comes into contact with the yarn contact surface of the contact body 11 at a predetermined position of the contact body 11. A predetermined tension is applied to the running yarn $Y_O$ by the tension control device 4 (FIG. 1). Thus, the yarn $Y_O$ is caused to run while in contact with the yarn contact surface of the contact body 11 under the predetermined tension. In this operation, if the tension, and consequently the contact pressure of the yarn on the contact body 11, is controlled so that it is at an appropriate level, the configuration of the yarn $Y_O$ is changed to a ribbon-like shape $Y_1$ in the noninterlaced portion where the yarn is not interlaced or hardly interlaced, but the interlaced portion of the yarn $Y_O$ where the interlacing degree is high runs in the entangled state without change of the configuration to a ribbon-like shape. Changes of the configuration are thus caused in the running yarn by the contact with the contact body for the reasons set forth hereinbefore. Namely, when an interlaced yarn is caused to run while being in contact with the contact body 11, in the interlaced yarn, the bundle of the individual filaments are forced to spread laterally to the running direction in a plane defined by the yarn contact surface of the contact body. However, since the individual filaments of the interlaced yarn are entangled and interlaced with one another, whether or not the above-mentioned change of the configuration to a ribbon-like shape is caused in the interlaced yarn depends on whether or not this spreading force is larger than the force necessary for releasing the entanglement. More specifically, in the noninterlaced portion, the entanglement is released by a small force because the degree of entanglement or interlacing is low. On the other hand, in the interlaced portion, the degree of entanglement or interlacing is high and a large force is necessary for releasing the entanglement. In the instant specification and appended claims, by the term "predetermined contact pressure" is meant a control pressure within such a range as will cause the above-mentioned change of the configuration in the noninterlaced portion of the yarn but will not cause the change of the configuration in the interlaced portion of the yarn. This contact pressure varies depending on such factors as the degree of interlacing and the thickness of the individual filaments and the yarn be tested. As will be apparent from the experiments described hereinafter, it was confirmed that results which are completely in agreement with results of the measurement of the degree of interlacing according to the hook-drop test method can be obtained when the contact pressure is in the range of from 2 to 20 g.

In the above mentioned embodiment, the contact body 11 having a yarn contact surface of a circular section with respect to the yarn running direction is illustrated. As will be apparent from the above mentioned illustration, the construction of the contact body 11 is not limited to one illustrated in the above mentioned embodiment. Namely, the configuration of the contact body 11 is not particularly critical in the present invention, so long as the yarn contact surface of the contact body 11 is such that the individual filaments of the yarn are effectively spread laterally on the yarn contact surface in a direction at a right angle to the running direction of the yarn by the contact pressure of the yarn on the contact body 11. In the present invention, it is preferred to use a contact body 11 in which the yarn contact surface is convex with respect to the running direction of the yarn. The number of such convex portions is not limited to one, but a plurality of convex portions may be formed at appropriate intervals.

As will be understood from the foregoing illustration, the change of the configuration of the yarn $Y_O$ occurs in the widthwise direction. Accordingly, this change of the configuration can be determined according to various measurement methods. As will also be understood from the foregoing illustration, interlaced portions of the yarn can be detected from the results of the measurement of the change of the configuration of the yarn. One of the simplest methods is one in which the measurement is carried out by visual inspection of an inspector. As shown in FIG. 2A, the interlaced portion of the yarn appears in the form resembling a knot in a ribbon and, therefore, it can easily be detected by visual inspection.

The structure and functional effect of the apparatus of the present invention illustrated in FIGS. 1A, 1B and 1C will now be described in detail. As will be apparent from the above mentioned brief summary, the yarn $Y_O$ to be tested is taken up by the take-up device 7 under a predetermined tension imparted by the tension control device 4, and interlaced portions of the yarn are detected by the interlaced portion detecting zone 10 illustrated in detail in FIGS. 2A and 2B.

The interlaced portion detecting zone 10 is arranged so that the yarn $Y_O$ is caused to come into contact with the contact body 11 at a predetermined position of the contact body 11 by means of guides 12. The light source 14 and light receiving device 13 are disposed to confront each other with the contact body 11 being interposed therebetween, so that the light axis intersects the contact portion. A slit 15 extending in the running direction of the yarn at a right angle is formed on the front surface of the light receiving device 13.

When the yarn $Y_O$ runs through the interlaced portion detecting zone 10 having the above-mentioned structure, a change of the configuration, such as mentioned above, is caused in the widthwise direction in the yarn $Y_O$, and by this change of the configuration, the quantity of light transmitted from the light source 14 to the light receiving device 13 is changed.

The light receiving device 13 is a photo-electric transducer which converts a received photo signal to an electric signal the level of which corresponds to the amount of light of the received photo signal. The photo receiving device 13 may be constructed by using a photodiode, a phototransistor, a photoelectric tube, a solar battery or the like. In this embodiment, as shown in FIG. 1B, the photo receiving device 13 consists of a photodiode 13a and a load resistor 13b, and the light radiated from the light source 14 is input to the photodiode 13a through the contact member 11 and yarn $Y_O$. Therefore, when the amount of the light received by the light receiving device 13 is changed in accordance with the change of the amount of light transmitted from the light source 14, an analog signal $S_1$ can be produced from the light receiving device 13, and the level $L_1$ of the signal $S_1$, as shown in FIG. 3A varies depending on the change of the amount of light transmitted from the light source 14.

The direct current component of the analog signal $S_1$ depends upon the intensity of the background-light issued from the light source 14 or the like and the alternating current component of the analog signal $S_1$ depends upon the variable intensity of light which corresponds to the change of the configuration of the interlaced yarn. The apex of the waveform of this alternating current component corresponds to an interlaced portion of the interlaced yarn.

In order to produce a pulse train consisting of pulses developed in response to the interlaced portions of the yarn by using the analog signal $S_1$, the analog signal $S_1$ is applied to the waveform processing circuit 23, which is illustrated in detail in FIG. 1C. In the waveform processing circuit 23, after the analog signal $S_1$ is amplified by an amplifier 23a, the direct current component of the analog signal $S_1$ is removed from the analog signal $S_1$ by a capacitor 23b, and as a result, only an alternating current component signal $S_2$ (shown in FIG. 3B) of the analog signal $S_1$ is applied to one input terminal of a comparator 23c. To the other input terminal of the comparator 23b, a comparing signal $S_5$ having a predetermined level $V_s$ is applied. The level $L_2$ of the alternating current component signal $S_2$ is compared with the level $V_s$ of the comparing signal $S_5$ in the comparator 23c, and only when the level $L_2$ is more than the level $V_s$, a level $L_3$ of an output signal $S_3$ from the comparator 23c becomes high level. As a result, the portion corresponding to the apex of the waveform of this alternating current component signal (see the hatched portion in FIG. 3B), is obtained as a series of pulses having a waveform shown in FIG. 3c. The output signal $S_3$ is applied to a one-shot multivibrator circuit 23. In the circuit 23d the signal $S_3$ is converted to a pulse signal $S_4$ as shown in FIG. 3D in which the pulse width of each pulse is a constant value, and the signal $S_4$ is applied to the pulse counter 24. Therefore, the counter 24 increases its count by one every time an interlaced portion in the yarn Yo passes through the interlaced portion detecting zone 10. As a result, the counter 24 can count the number of the interlaced portions passing through the interlaced portion detecting zone 10. In the above-mentioned embodiment, although the output signal $S_3$ produced from the comparator 23c is applied to the counter 24 through the one-shot multivibrator circuit 23d, it is possible to directly apply the signal $S_3$ to the counter 24.

As will be apparent to those skilled in the art, the degree of interlacing or coherency factor can be determined from the number of the counted pulses and the length of the yarn along which the measurement is effected.

Any tension control means capable of being applied to the above-mentioned measurement method and imparting a predetermined tension to the yarn can be used in the present invention. In the above mentioned embodiment, a glass sheet provided with a circular cross-section is used as the contact body 11. In the present invention, the intended function can be obtained if only the yarn contact portion or surrounding portion has a light-transmitting property. In the above mentioned embodiment, a slit is formed on the light receiving device 13, but this slit can be omitted if the light-transmitting portion of the contact body 11 is used instead of the slit. However, the shape of the slit is not particularly critical, and the same function can be attained by a fine aperture or a slit extending in the widthwise direction and the interlaced portion of the yarn can be detected stably. The guides 12 are effective for forming a stable yarn passage so that interlaced portions can be detected stably, but the guides 12 need not be formed in the interlaced portion detecting zone 10.

Based on the results of experiments conducted by the inventors, in order to eliminate undesired effects caused by background light, it is preferable that the size of the slit be based on the thickness of the yarn as shown in the following table 1.

Table 1

| Thickness of the yarn [de] | Size of the slit [mm] |
|---|---|
| 50 to 100 | 0.2 × 0.3 |
| 100 to 200 | 0.3 × 0.4 |

Experiments conducted by using the apparatus of the present invention having the above-mentioned structure and the conventional hook-drop test system will now be described.

Experiment 1

Degrees of interlacing in various interlaced multifilament yarns were determined by using the apparatus of the above-mentioned embodiment and the results obtained were compared with the results obtained by the measurement according to the conventional hook-drop test method. The measurement was conducted under the following conditions.

(1) Yarn running speed: 120 m/min
(2) Yarn tension: 10 g
(3) Measurement time: 5 seconds Obtained results are shown in Table 2.

Table 2

| | Degree of Interlacing | |
|---|---|---|
| Yarns Tested | Conventional hook-drop test method | Method of present invention |
| 100 denier/25 filaments acetate yarn | 43 | 41 |
| 50 denier/24 filaments polyester yarn | 39 | 37 |
| 175 denier/72 filaments polyester yarn | 52 | 50 |

Note: The degree of interlacing was calculated according to the formula:

$$DI = NI/LY$$

wherein DI represents the degree of interlacing, NI represents the number of interlaced portions counted during the measurement time, and LY represents the length (m) of the yarn passing through the contact body during the measurement time.

Experiment 2

Various 50 denier/25 multifilament polyester yarns differing in the degree of interlacing were tested according to the method of the present invention, and the results obtained were compared with the results obtained according to the conventional hook-drop test method. The measurement was carried out under the same conditions as adopted in Experiment 1. The obtained results are shown in Table 3.

Table 3

| | Number of Interlaced Portions | |
|---|---|---|
| Sample No. | Conventional hook-drop test method | Method of present invention |
| 1 | 28 | 26 |
| 2 | 38 | 37 |
| 3 | 62 | 61 |

An embodiment, in which means for measuring the length of the running interlaced multifilament yarn is attached to the above-mentioned apparatus and the degree of interlacing is automatically determined, will now be described with reference to FIGS. 4A, 4B and 5. Descriptions of elements disclosed in the above-mentioned first embodiment are omitted unless a particular mention is necessary. Accordingly, the elements having the same function as the elements of the first embodiment are indicated by the same reference numerals.

Figure 4A:
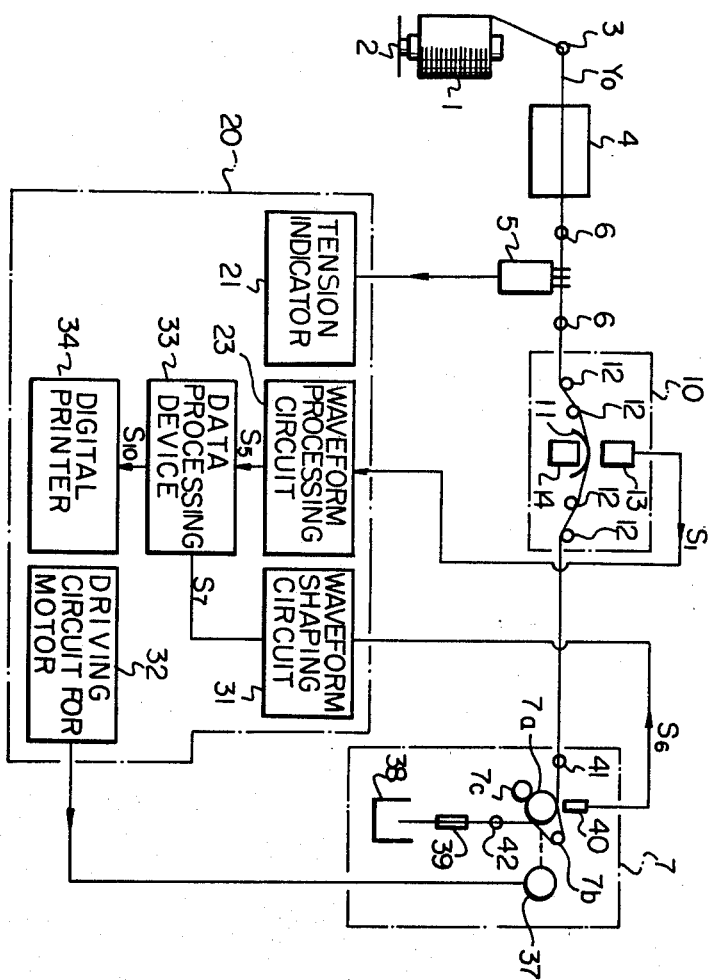
FIG. 4A is a schematic drawing indicating the essential elements of the other embodiments of the apparatus according to the present invention.
Figure 4B:
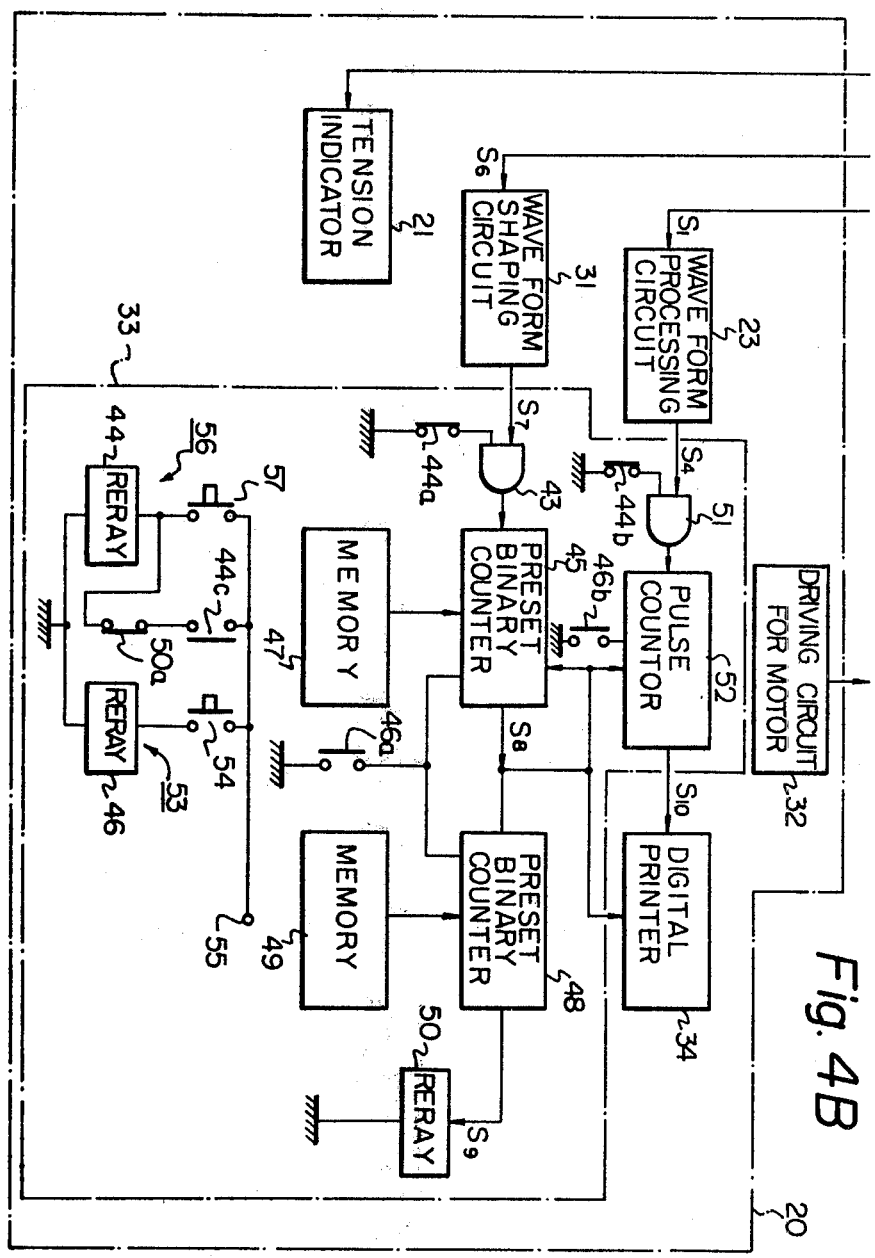
FIG. 4B is a block diagram of the essential portions of the electric circuit utilized for the apparatus illustrated in FIG. 4A.

In the apparatus shown in FIGS. 4A and 4B, a body portion 20 of the measurement apparatus comprises a tension indicator 21, a motor driving circuit 32, a waveform processing circuit 23, a data processing device 33 and a digital printer 34. Electric power is supplied to each of these elements from a power source device (not shown). A take-up device 7 comprises:

a roller 7a having a chromium-plated mirror plane surface and being rotated by an electric motor 37 driven by the driving circuit 32;

a separate roller 7b having a chromium-plated mirror plane surface and being rotatably supported in the vicinity of the roller 7a;

a capstan roller 7c having a surface coated with a rubber material and being rotatably supported to have contact with the roller 7a with a certain contact pressure;

a yarn discharge aspirator 39 for taking up a yarn $Y_O$ fed from said three rollers and discharging the yarn into a waste yarn box 38, to which aspirator compressed air is supplied through a compressed air tube (not shown);

a yarn guide 41 for setting and fixing a yarn passage for the yarn introduced in said discharge aspirator 39 from said rollers, and;

the waste yarn box 38.

Accordingly, the passage for the yarn $Y_O$ is set and fixed by the guide 41, and the yarn $Y_O$ is wound by several turns on the roller 7a and separate roller 7b and pressed by the capstan roller 7c. In this state, the yarn $Y_O$ is taken up at a constant speed and discharged into the waste yarn box 38 by the discharge aspirator 39.

In order to develop an electric signal related to the number of rotations of the roller 7a, in the take-up device 7, a conventional rotating signal generator is provided. The rotating signal generator comprises a magnetic toothed-wheel body (not shown in FIGS. 4A and 4B) rotating with the roller 7a and an electromagnetic pick-up device 40 located adjacent to the toothed-wheel body. The generator electromagnetically generates an alternating current signal $S_6$, the frequency of which varies depending on the change in the number of rotations of the roller 7a.

The alternating current signal $S_6$ is applied to a waveform shaping circuit 31 in the data processing device 33 to shape the waveform of the signal $S_6$ in the form of a square wave. The output signal $S_7$ from the circuit 31 is applied to one input terminal of an AND gate 43. A normally closed switch 44a which is open when a relay 44 is energized, is connected between the other input terminal of the AND gate 43 and earth, and the output signal $S_7$ is applied to a preset binary counter 45 as a count down pulse signal only when the switch 44a is open. The preset binary counter 45 is preset when a normally open switch 46a, which is closed only when a relay 46 is energized, is closed, and the contents in a memory 47 is set in the preset binary counter 45. Therefore, when the counter 45 starts the count-down operation after the preset operation by the switch 46a, the counter 45 develops a borrow signal $S_8$ at the time when the content of the counter 45 becomes zero, that is, when the number of the count down pulses applied to the counter 45 is equal to the number corresponding to the contents of the memory 47. Consequently, assuming that the number of the teeth of the teeth-wheel is N and the peripheral length of the roller 7a is l[m], it follows that the count down pulse is developed every time when the yarn $Y_O$ is taken up by the length of l/N[m]. As a result, if the content of the memory 47 is ION/l, the borrow signal $S_8$ can be produced when the yarn $Y_O$ is taken up by 10 [m]. The borrow signal $S_8$ is applied to an another preset binary counter 48 as a count down pulse. The preset binary counter 48 is also preset when the switch 46a is closed and at this time the content of a memory 49 is preset in the counter 48. In the memory 49, the number of measuring operation is stored, and the preset binary counter 48 develops a borrow signal $S_9$ at the time when the contents of the counter 48 becomes zero by the application of the signal $S_8$. When the borrow signal $S_9$ is developed, a relay 50 is actuated by the signal $S_9$, and a normally closed switch 50a is open.

On the other hand, the signal $S_1$ from the light receiving device 13 is applied to the waveform processing circuit 23 constructed the same as the circuit 23 shown in FIG. 1A, and the pulse signal $S_4$ is developed from the waveform processing device 23. The signal $S_4$ is applied to one input terminal of an AND gate 51 in the data processing device 33. The other input terminal of the AND gate 51 is grounded through a normally closed switch 44b which is open when the relay 44 is energized. The signal $S_4$ passes through the AND gate 51 only when the switch 44b is open, and is applied to a pulse counter 52 as a series of count up pulses. The pulse counter 52 is reset by the application of the signal $S_8$ or by closing a normally open switch 46b which is closed when the relay 46 is energized. The counted data $S_{10}$ from the pulse counter 52 is applied to the digital printer 34, and the printer 34 prints out the contents of the data $S_{10}$ in decimal numbers when the signal $S_8$ is applied to the printer 34.

In order to set the data processing device 33 in the initial condition prior to start the measuring operation, there is provided a reset circuit 53 in the body portion 20. The reset circuit 53 consists of the relay 46 and a push-button switch 54, and the relay 46 and the push-button switch 54 are connected in series between a power supply terminal 55 and ground. Therefore, pushing the push-button switch 54 energizes the relay 46, and the switches 46a and 46b are closed to reset the binary counter 52 and to preset the preset binary counters 45 and 48. In the body portion moreover, a starting circuit 56 is arranged, which is used thereby placing the data processing device 33 in an operable condition. The starting circuit 56 involves the relay 44, and the relay 44 is connected to the power supply terminal 55 through a push-button switch 57. A normally open switch 44c, which is closed only when the relay 44 is energized, is connected in series to the switch 50a, and the series circuit of the switches 50a and 44c is connected in parallel to the push-button switch 57. Therefore, when the push-button switch 57 is closed under the condition that the switch 50a is closed, the relay 44 is energized and the switch 44c is closed. As a result of this, the relay 44 remains energized even when the switch 57 is open. Consequently, at the same time, the switches 44a and 44b are also kept in the open condition as long as the relay 50 is not energized. Therefore, as will be understood, each of the AND gates 43 and 51 permits each of the signals $S_7$ and $S_4$ to pass through, respectively, from the moment the switch 57 is closed to the moment the relay 50 is energized.

The operation of the body portion 20 will be hereinafter explained.

When the switch 54 is operated, the switches 46a and 46b are actuated, the pulse counter 52 is reset and the preset binary counters 45, 48 are preset. As a result, the contents of the memory 47, which decides the length of the yarn $Y_O$ to be measured at one, is preset in the counter 45, and on the other hand, the contents of the memory 47 which decides the number of the measuring time is preset in the counters 48. When the switch 57 is closed, the AND gates 51 and 43 are opened, so that the signals $S_4$ and $S_7$ are applied to the pulse counter 52 and the preset binary counter 45, respectively. Then, the pulse counter 52 starts counting up the pulses obtained from the waveform processing circuit 23, and the counted result in the counter 52 is sent to the printer 34. On the other hand, at the same time, the preset binary counter 45 starts the counting-down operation by the application of the signal $S_7$. Since the content of the memory 47 is decided as described above, at the time the yarn $Y_O$ has been taken the predetermined length after the AND gates 51 and 43 are open, the borrow signal $S_8$ is developed. As a result of this, the printer 34 is actuated so that the contents of the binary counter 52 at this time are printed out and the counter 52 is reset by the application of the borrow signal $S_8$. Consequently, the data printed out by the printer 34 means the number of interlaced portions per a predetermined length of the yarn $Y_O$. That is, the degree of interlacing is automatically obtained from the printer 34. In addition, by the borrow signal $S_8$, the preset binary counter 48 is counted down by 1, and at the same time, the preset binary counter 45 is preset. After the reset operation of the counter 52 and the preset operation of the counter 45 have been effected as described above, the same operation as that described above is repeated. This operation is repeated until the content of the counter 48 becomes zero. That is, when the content of the counter 48 becomes zero, the borrow signal $S_9$ is developed so that the relay 50 is actuated, and the switch 50a is open. Therefore, the energized condition of the relay 44 is released so that the switches 44a and 44b are closed, and a series of the operation of the data processing device 33 has finished. The number of repeating operations, in other words, the number of the output data obtained from printer 34, depends upon the number stored in the processed 49. Therefore, it is possible to easily calculate the average of the degree of interlacing by using the results of the data obtained from the printer 34.

In this embodiment, although the data processing device 33 shown in FIGS. 4A, 4B is used for processing the signals $S_4$ and $S_7$, the signals $S_4$ and $S_7$ may be processed by using a small size computer instead of the device 33.

If a small size computer is used, it is also possible to construct the data processing device 33 in such a way that various statistical data required for quality control, such as the value of standard deviation and the value of dispersion, can be automatically printed out on the basis of the data signal $S_{10}$.

In the foregoing embodiment, a yarn length measuring means comprising the electromagnetic pick-up device 40 and the yarn length measuring device 33 is illustrated. In the present invention, the yarn length measuring means is not limited to this combination and any means capable of measuring the length of a sample yarn may be used in the present invention. For example, when a constant speed winder is used as the take-up device 7, a timer or other known measuring means can be used. Further, if the length of a sample yarn is preset to a certain value or if marks are put on a sample yarn at a predetermined interval and the degree of interlacing is determined along the predetermined length between two marks, the above-mentioned yarn length measuring means need not be used.

The apparatus of the present invention has been illustrated as an apparatus for determining the degree of interlacing. However, as will be apparent to those skilled in the art, if the computing processing means is appropriately arranged, the apparatus of the present invention can be used for determining the coherency factor based on the average yarn length between interlaced portions. This embodiment is also included within the scope of the present invention.

According to the present invention, a detecting needle need not be inserted into an interlaced multifilament yarn to be testd and the degree of interlacing can be determined only by causing the yarn to run while having contact with the contact body. In this point, the present invention can be clearly distinguished over the conventional hook-drop test method. By virtue of this characteristic feature, according to the present invention, it is possible to determine the degree of interlacing even in case of a yarn running at a high speed, and the measuring operation can be remarkably and effectively rationalized. For example, in each of the apparatuses illustrated in the above-mentioned embodiments, the measurement can be carried out stably when the running speed of the yarn is up to about 1200 m/min. Further, according to the present invention, a sample yarn is only temporarily deformed for the measurement and the yarn is not damaged at all by the measurement. Then, as will be described later, on-line inspection of the degree of interlacing during the manufacturing process becomes possible. Still further, since a signal proportional to the interlacing density can be obtained as an output signal, a quality information during the manufacturing process, which cannot be obtained according to the conventional method, can be effectively attained. In addition, if the output signal is put into the control device and the computing, storing and data-processing device, the measurement operation can be accomplished completely automatically.

In the above-mentioned embodiments, apparatuses for determining the degree of interlacing in interlaced multifilament yarns have been illustrated. An embodiment shown in FIGS. 5 to 7 relates to an apparatus for inspecting the interlaced yarn manufacturing process. This apparatus is arranged so that it can easily and simply be attached to respective processing spindles of an interlacing machine having a plurality of processing units.

Figure 5:
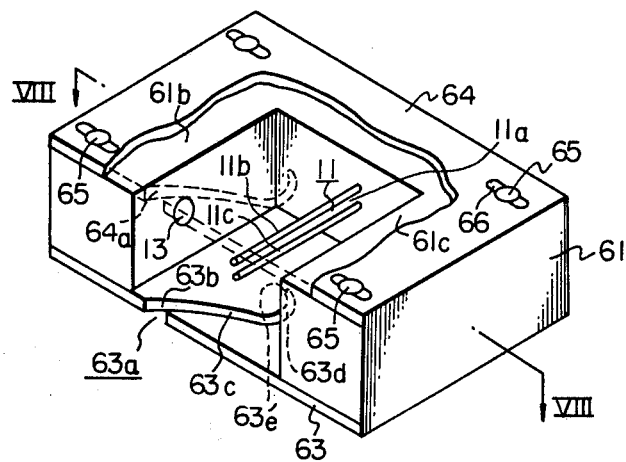
FIG. 5 is a schematic perspective view of a detecting unit utilized for the apparatus for inspecting the interlaced yarn manufacturing process.
Figure 6:
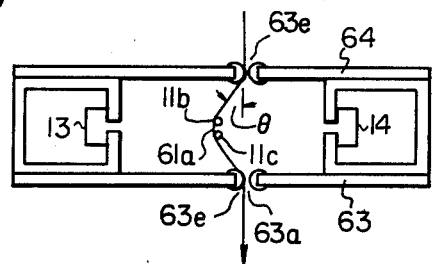
FIG. 6 is a schematic side view of the detecting unit illustrated in FIG. 5.
Figure 7:
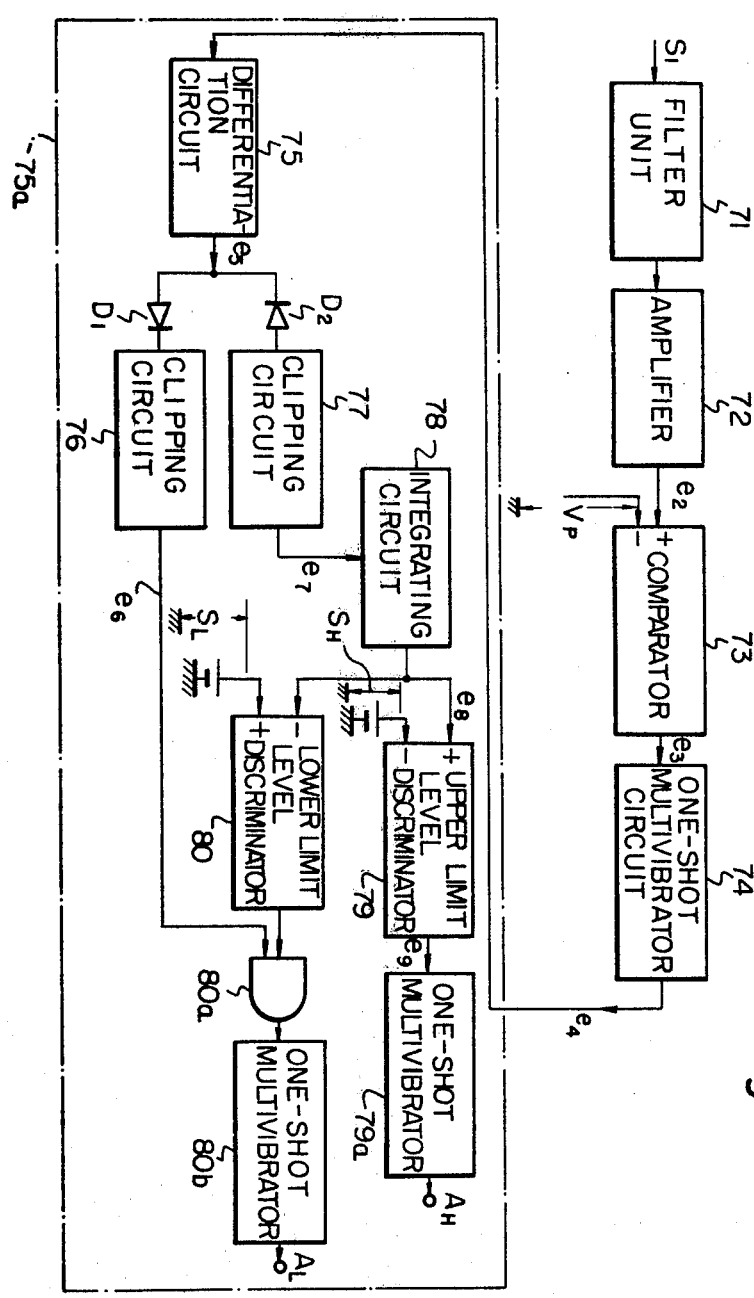
FIG. 7 is a block diagram of the converting the signal issued from the light receiving element to a time series pulse signal, which is utilized for a modified embodiment of the apparatus according to the present invention, FIG. 8 sets forth explanation diagrams indicating the relation between the respective upstream time series signal and a time series signal converted therefrom, which signals are issued from the corresponding electrical elements illustrated in FIG. 7.

Referring to FIGS. 5 and 6, a contact body 11 composed of a hard porcelain is disposed in the central portion of a bottom side 61c of a concave case 61 in parallel to both the sides 61b and 61c of the case 61. This yarn contact body 11 comprises two yarn contact portions 11b and 11c having contact with the yarn $Y_O$ through a gap 11a extending in the running direction of the yarn. On the insides of both the sides 61b and 61c of the case 61 there is disposed a light receiving element 13 and a light emitting element 14 so that they confront each other and the light axis between them passes through the above-mentioned gap 11a of the contact body 11. Yarn guide plates 63 and 64 are attached to the top and bottom faces of the case 61 by screws 65 inserted into long holes 66 formed in the yarn guide plates 63 and 64. On the yarn guide plate 63, a yarn guide notch 63a for guiding the yarn $Y_O$ is formed. The yarn guide notch 63a comprises a yarn introducing opening 63b and a yarn guide 63d which are disposed on the opposite to vertical plane including the contact body 11, and a yarn guiding portion 63c which connects the yarn introducing opening 63b to the yarn guide 63d. A yarn guide tip 63e, which is composed of hard porcelain and has a groove 63e for guiding the running yarn $Y_O$, is attached to the yarn guide portion 63d to prevent the yarn from being damaged. Also on the yarn guide plate 64, a similar yarn guide notch 64a, to the notch 63a is formed. Electric circuits such as interlaced portion detecting circuit 20 and alarm circuit 80 described hereinafter are set on the bottom side 61a of the case 61.

The yarn $Y_O$ is set on the yarn guide plates 63 and 64 so that the yarn $Y_O$ is located on the yarn introducing openings 63b and 64b of the guide notches 63a and 64a of the guide plates 63 and 64, and then, the interlacing operation is initiated. The yarn $Y_O$ passes through the yarn inducing portions 63c and 64c of the guide notches 63a and 64a and arrives at the yarn guide portions 63d and 64d, and the yarn is caused to run while being automatically bent as shown in FIG. 6. Accordingly, the operation of setting the yarn on the yarn guide plates 63 and 64 can be accomplished very simply.

When the apparatus having the above-mentioned structure is disposed in a take-up passage of a interlaced yarn in a processing spindle unit of the interlacing machine, and the yarn $Y_O$ is caused to run while being bent in the above-mentioned manner, a pressing contact force F is imparted to the yarn $Y_O$. The pressing contact force is expressed by the formula:

$$F = 2T \sin(\theta/2)$$

wherein T stands for a tension imposed on the yarn $Y_O$, which is determined by the processing conditions, and $\theta$ stands for the yarn bending angle of a bent passage formed in the apparatus to cause the yarn $Y_O$ to contact the contact body 11. If the bending angle $\theta$ is adjusted by shifting in the lateral direction the positions of attaching the guide plates 63 and 64 through long holes, the pressing contact force F can be controlled independently from the tension T.

In this embodiment, since the interlaced yarn $Y_O$ comes into contact with two yarn contact portions 11b and 11c, the above-mentioned change of the configuration in the yarn $Y_O$ can be obtained in a stable condition. In addition, since the contact body 11, the light source 14 and the light receiving device 13 are incorporated in the case 61, even if the contact body 11 is caused to vibrate by the effect of the vibration of the main machine, the contact body 11 vibrates together with the light source 14 and the light receiving device 13. Therefore, it is possible to obtain the desired signal according to the interlacing portion of the yarn from the light receiving device 13 in a stable condition.

The present embodiment is different from the above-mentioned two embodiments in the point that it is judged from variations of the time between two adjacent pulses whether or not the interlaced portions are formed at desirable time intervals. This feature will now be described in detail with reference to FIG. 7.

The signal issued from the light receiving device 13 is an output signal $S_1$ corresponding to the abovementioned change of the configuration of the yarn, and this signal is treated in the following manner.

High frequency noise is removed from the output signal $S_1$ by a filter unit 71 and, then, the signal is amplified by an amplifier 72 to obtain a detection signal $e_2$ of a predetermined level. The peak of the detection signal $e_2$ corresponds to an interlaced portion of the yarn $Y_O$.

The level of the detection signal $e_2$ is compared with a predetermined comparing level Vp in a comparator 73 (FIG. 8A), and as a result, an interlaced portion signal $e_3$ as shown in FIG. 8B is obtained from the comparator 73. The width of each pulse of this signal $e_3$ corresponds to the size of the interlaced portion of the yarn $Y_O$ and the pulse interval corresponds to the interval between two interlaced portions.

Moreover, the interlaced portion signal $e_3$ which consists of a series of pulses is applied to a one-shot multivibrator circuit 74 to obtain a pulse signal $e_4$ as shown in FIG. 8C. Since the operation of the one-shot multivibrator 74 is the same as that of the one-shot multivibrator 23d in FIG. 1C, the detailed description of the operation of the one-shot multivibrator 74 will be omitted. The signal $e_4$ produced from the one-shot multivibrator circuit 74 is applied to a differentiation circuit 75 to obtain a differentiated signal $e_5$ as shown in FIG. 8D, and the signal $e_5$ is rectified by diodes $D_1$ and $D_2$, respectively. Therefore, only the positive polarity component of the signal $e_5$ can be derived by the diode $D_1$ and, on the other hand, only the negative polarity component of the signal $e_5$ can be derived by the diode $D_2$. Each of the output signals from the diodes $D_1$ and $D_2$ is applied to each of clipping circuits 76 and 77, respectively. The clipping circuit 76 is the circuit which clips the positive peak value of the positive polarity component of the signal $e_5$ so as to prevent the positive peak value from exceeding a predetermined level. The clipping circuit 77 is the circuit which clips the negative peak value of the negative polarity component of the signal $e_5$ so as to prevent the negative peak value from becoming under a predetermined level. In FIGS. 8E and 8F, the output signal $e_6$ from the clipping circuit 76 and the output signal $e_7$ from the clipping circuit 77 are shown, respectively.

An integrating circuit 78 is arranged so that certain values are always integrated, and it is reset by the application of the signal $e_7$ at the time of the falling of the pulse of the signal $e_4$. Accordingly, the integrated output signal $e_8$ of the integrating circuit 78 has a saw tooth wave form as shown in FIG. 8G and the peak value is proportional to the pulse interval of the interlaced portion signal $e_3$, namely the interval between interlaced portions in the yarn $Y_O$. The integrated output signal $e_8$ is put into an upper limit level discriminator circuit 79 and a lower limit level discriminator circuit 80. The upper limit level discriminator circuit 79 is arranged so that it puts out a signal when the integrated output signal $e_8$ exceeds an upper limit threshold level SH. The circuit 79 can be arranged by using a comparator. Accordingly, when the interval between two adjacent interlaced portions in the yarn $Y_O$ exceeds a predetermined length, a signal $e_9$ issued from the upper Limit Level Discriminator 79 is input to a One-Shot Multivibrator 79a so that a signal AH is created thereby. The lower limit level discriminator circuit 80 is arranged so that the level of the output of the lower limit level discriminated circuit 80 becomes low when the signal $e_8$ exceeds a lower limit threshold level SL. The circuit 80 can be arranged by using a comparator.

The output signal from the circuit 80 is applied to one input terminal of an AND gate 80a, and the signal $e_6$ is applied to the other input terminal of the AND gate 80A. Therefore, the signal with high level can be obtained from AND gate 80a only when the integrated output signal $e_8$ is below the lower threshold lever SL (FIG. 7) at the time of the rising of the pulse of the signal $e_4$. As a result, when the signal with high level is obtained from the AND gate 80a, a one-shot multivibrator circuit 80b is triggered and it produces a lower limit alarm signal AL with a narrow pulse width as shown in FIG. 8I. Accordingly, a lower limit alarm signal A1 (FIG. 7) is put out when the interval between interlaced portions in the yarn $Y_O$ is below the predetermined region. Thus, an alarm circuit 75a can inspect intervals between every two adjacent interlaced portions in the yarn $Y_O$.

In the above described circuit arrangement, breakage of the yarn $Y_O$ is detected as the upper limit alarm AH. Therefore, yarn breakage can be detected without provision of any particular circuit. Moreover, a counting circuit need not be laid out for determining the degree of interlacing. Therefore, the circuit structure can be remarkably simplified and the circuit can easily be set in the case 61. In the case where the degree of interlacing is determined for inspection of the manufacturing process, since the yarn length should be measured, it is impossible to obtain a response when trouble takes place. In the present embodiment, occurrence of trouble can be detected very promptly, and the quantity of the waste yarn can be remarkably reduced when any trouble takes place. Therefore, the present embodiment is especially effective for detection of yarn breakage.

In the foregoing illustration, the embodiment is applied to inspection of the manufacturing process. Needless to say, the embodiment can also be applied to detection of the interlaced portions in an apparatus for determining the degree of interlacing. In this case, a counting circuit for counting the interlaced portion signal $e_4$ should be laid out instead of or in parallel to the alarm circuit 75a.

In the foregoing illustration, occurrence of trouble such as yarn breakage is indicated by an alarm. If a cutter is actuated by the alarm output, the trouble can be eliminated in each spindle of the manufacturing machine independently. Further, if the interlaced portion detecting signal $e_2$ is put into an interlacing degree determining counter circuit formed in an integrated inspection chamber, all the process steps can be inspected and controlled in an integrated manner. Similarly, the alarm outputs AH and AL of the alarm circuit 75a can be controlled in an integrated manner.

Figure 9A:
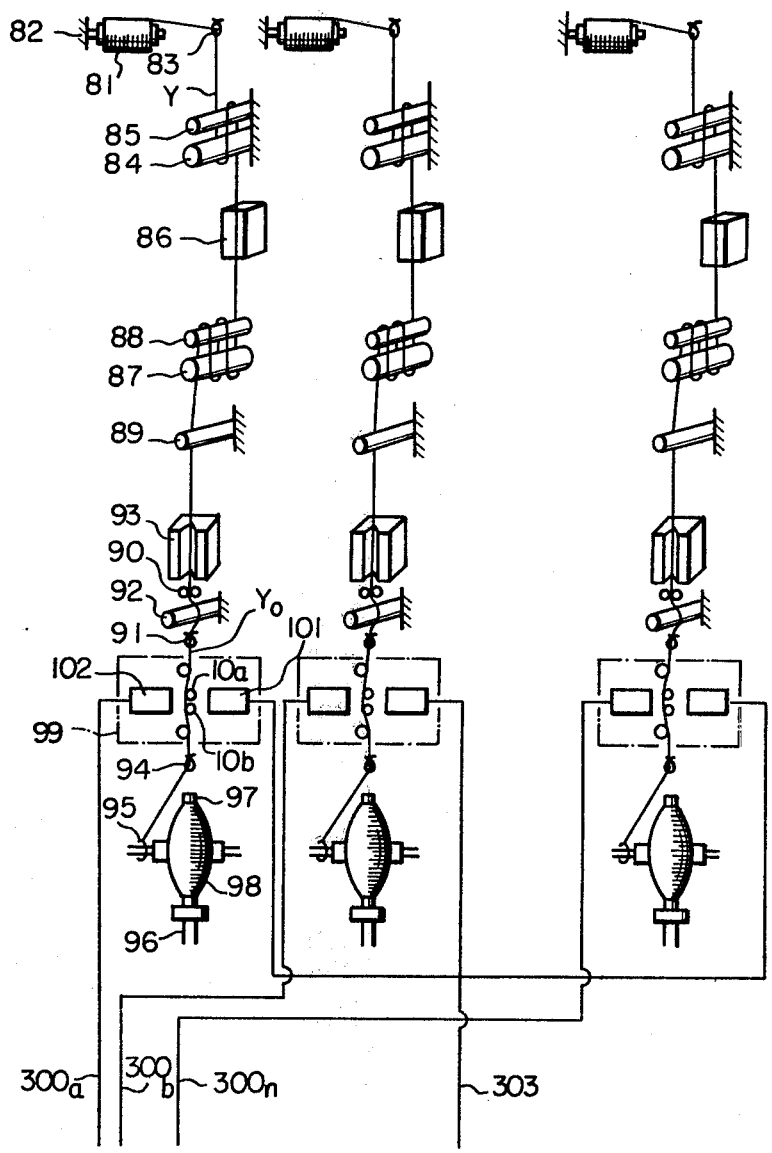
FIG. 9A is a schematic front view of a machine provided with a plurality of interlacing units, each unit being provided with the measuring device according to the present invention.
Figure 9B:
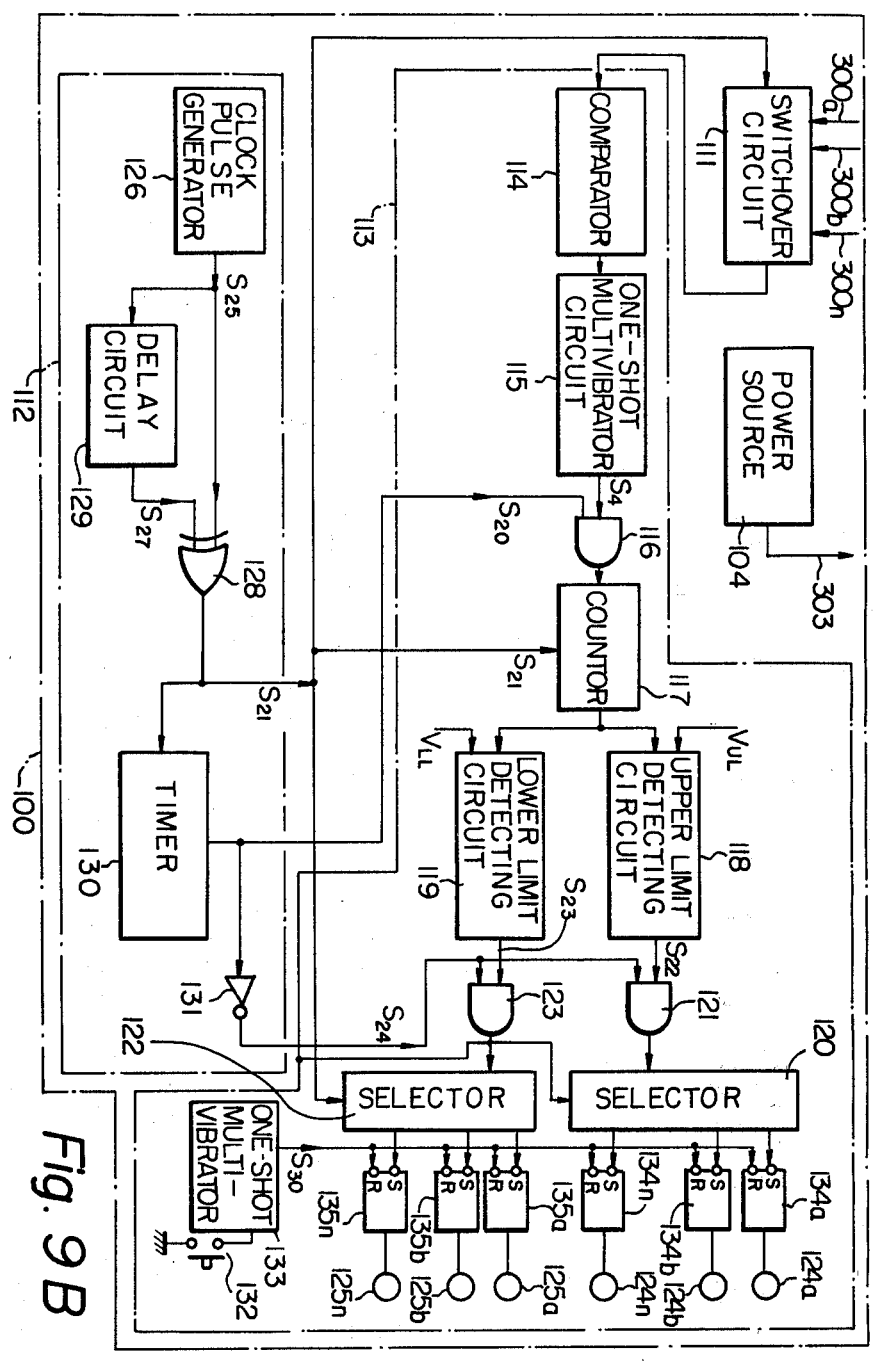
FIG. 9B is a block diagram of essential electric elements adopted for the measuring units illustrated in FIG. 9A.

In FIGS. 9A and 9B, an embodiment is illustrated wherein the apparatus for measuring the degree of interlacing in interlaced multifilament yarns according to the present invention is adopted for inspection of the manufacturing process. The measuring apparatus per se is not substantially different from the apparatus in the above-mentioned embodiments. Accordingly, illustration of the apparatus per se is omitted.

The manufacture of interlaced yarns by using a draw-false twisting machine will now be outlined with reference to FIGS. 9A and 9B. The draw-false twisting machine is arranged so that yarns can be simultaneously formed in a plurality of spindle units as shown in FIG. 9A. Since these spindle units have the same structure, the manufacturing process will be described with reference only to the spindle unit located farthest to the left.

An undrawn multifilament yarn Y is fed from a undrawn yarn package 81 supported on a yarn feed device 82, passes through a yarn guide 83 and is wound by one turn on a hot pin 84 maintained at a predetermined temperature and a snap pin 85. The yarn is drawn to a length several times the original length of the hot pin 84 and snap pin 85 and thermally set by a setting plate 86 maintained at a predetermined temperature. Then, the yarn is wound by several turns on a draw roller 87 and a separate roller 88. The multifilament yarn Y coming from the draw roller 87 and separate roller 88 passes through a yarn guide 89 and is caused to have frictional contact with a tension cut guide 92 disposed as a friction member between yarn guides 90 and 91 to reduce the yarn tension to from about ⅓ to about 1/5 of the winding tension. Under this reduced tension, the yarn is subjected to a fluid treatment by a fluid jet nozzle 93 disposed as interlacing means, whereby the yarn is entangled and interlaced. The entangled multifilament yarn Y, namely the interlaced yarn $Y_O$, passes through a yarn guide 94 and is wound on a bobbin 97 supported on a spindle 96 through a traveller 95. Thus, a product package 98 is formed. In the present embodiment, in each spindle unit of the interlaced yarn manifacturing machine, an interlacing degree detector 99 is disposed between the interlacing means 93 and the yarn guide 94 of the winding zone. The outputs of these detectors 99 can be inspected in an integrated manner by means of an integrated inspection panel 100, which will now be described.

Figure 10:
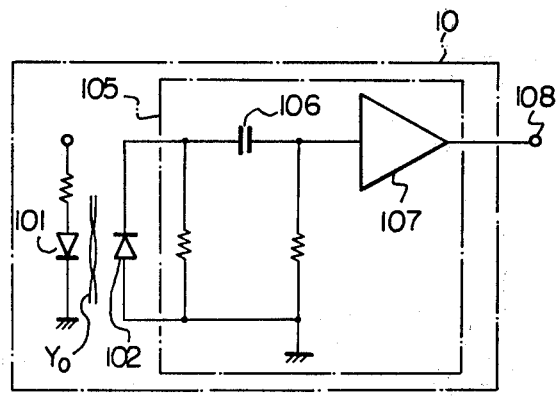
FIG. 10 is a schematic diagram of an electric circuit utilized for the light source and light receiving elements illustrated in FIG. 9A, FIG. 11 sets forth explanation diagrams indicating the relation between the respective upstream time series signal and a time series signal converted therefrom, which signals are issued from the corresponding electric elements illustrated in FIG. 9B.

As in the foregoing embodiments, the state of interlacing is determined from the change of the configuration of the yarn $Y_O$ on passage through the gap between contact rods 10a and 10b of the detector by means of a photoelectric detector comprising a light source and a light receiving device 102. Namely, the quantity of light transmitted to the light receiving device 102 from the light source 101, to which electric power is supplied from a power source 104 (FIG. 9B) disposed on the integrated inspection panel 100, is changed according to the change of the configuration of the yarn $Y_O$. Accordingly, the light receiving device 102 puts out an electric analog signal (comprising a direct current component and an alternating current component) corresponding to the change of the configuration of the yarn $Y_O$. This electric analog signal is transmitted to an output circuit 105, shown in FIG. 10, wherein the direct current component is cut off by a condenser 106 and the alternating current component alone is amplified by an amplifier 107 and put out from a terminal 108. This output signal is transmitted to a switchover circuit 111 (FIG. 9B) of the concentrated inspection panel 100 located on the side of the draw-false twisting machine or in an inspection room disposed in the manufacturing process area. The interlacing degree detectors 99 of the respective spindles are switched over in sequence by the switchover circuit 111 which is controlled by a control circuit 112. The output signal of the detector 99 selected by the switchover circuit 111 is applied to an abnormal condition detecting circuit 113 laid out on the integrated inspection panel 100 and, in a manner described below, the degree of interlacing is determined from this output signal and an alarm is given according to need.

The output signal from the switch over circuit 111 is processed by a comparator 114 and a one-shot multivibrator circuit 115 in the same manner as described with respect to FIG. 1C. Therefore, the pulse signal $S_4$, as shown in FIG. 3D, is obtained from the one-shot multivibrator circuit 115 and is applied to one input terminal of an AND gate 116. The AND gate permits the pulse signal $S_4$ to pass through only when the gate signal $S_{20}$ produced from the control circuit 112 is in a high level condition, and the number of the pulses which are produced during the time the gate is open is counted in a pulse counter 117 which is reset by the application of the timing pulse signal $S_{21}$ from the control circuit 112 just before the AND gate 116 is open. The counted value in the counter 117 is applied to an upper limit detecting circuit 118 and a lower limit detecting circuit 119, respectively. The upper limit detecting circuit 118 is constructed by using a magnitude comparator, and the counted value is compared with the upper limit value $V_{UL}$ applied to the upper limit detecting circuit 118. Then, the level of an output signal $S_{22}$ of the circuit 118 becomes a high level signal when the counted value exceeds over the value $V_{UL}$. On the other hand, the lower limit detecting circuit 119 is also constructed by using a magnitude comparator, and the counted value is compared with a lower limit value $V_{LL}$ applied to the lower limit detecting circuit 119. Then, the level of an output signal $S_{23}$ is a high level one when the counted value is below the lower limit value $V_{LL}$. The output signal $S_{22}$ is applied to a selector 120 through an AND gate 121 and the output signal $S_{23}$ is applied to a selector 122 through an AND gate 123. A gate signal $S_{24}$ is also applied to the AND gates 121 and 123 to control the AND gates 121 and 123.

Lamps 124a, 124b, ..., and 124n, corresponding to the spindles are connected to the output side of the selector 120 through R-S flip-flops 134a to 134n. The selector 120 is switched over so as to connect the output signal from the AND gates 121 to one of the lamps 124a through 124n in synchronization with the switchover operation of the switchover circuit 111. In the same manner, lamps 125a through 125n, corresponding to the spindles are connected to the output side of the selector 122 through R-S flip-flops 135a to 135n. The selector 122 is also switched over so as to connect the output signal from the AND gate 123 to one of the lamps 125a through 125n in synchronization with the switchover of the switchover circuit 111. These switchover operations of the selectors 120, 121 and the switchover circuit 111 are carried out by the application, of the timing pulse signal $S_{21}$ from the control circuit 112. The output lines from the selectors 120 and 122 are connected to the set terminals S of the R-S flip-flops, respectivley, and the output signal $S_{30}$ from the one-shot multivibrator 133 is applied to each reset terminal R of the R-S flip-flops 134a and 134n and 135a to 135n. By closing a push-button switch 132, the one-shot multivibrator 133 is triggered and the voltage level of the signal $S_{30}$ becomes high for a predetermined period. Lamps 124a to 124n and 125a to 125n are connected to the output terminals of the R-S flip-flops 134a to 134n and 135a to 135n, respectively. The voltage level of the output terminal of each R-S flip-flop becomes low when the push-button switch 132 is closed and, on the other hand, the voltage level of the output terminal of each R-S flip-flop becomes high when the high level signal is applied to the set terminal S thereof.

Figure 11:
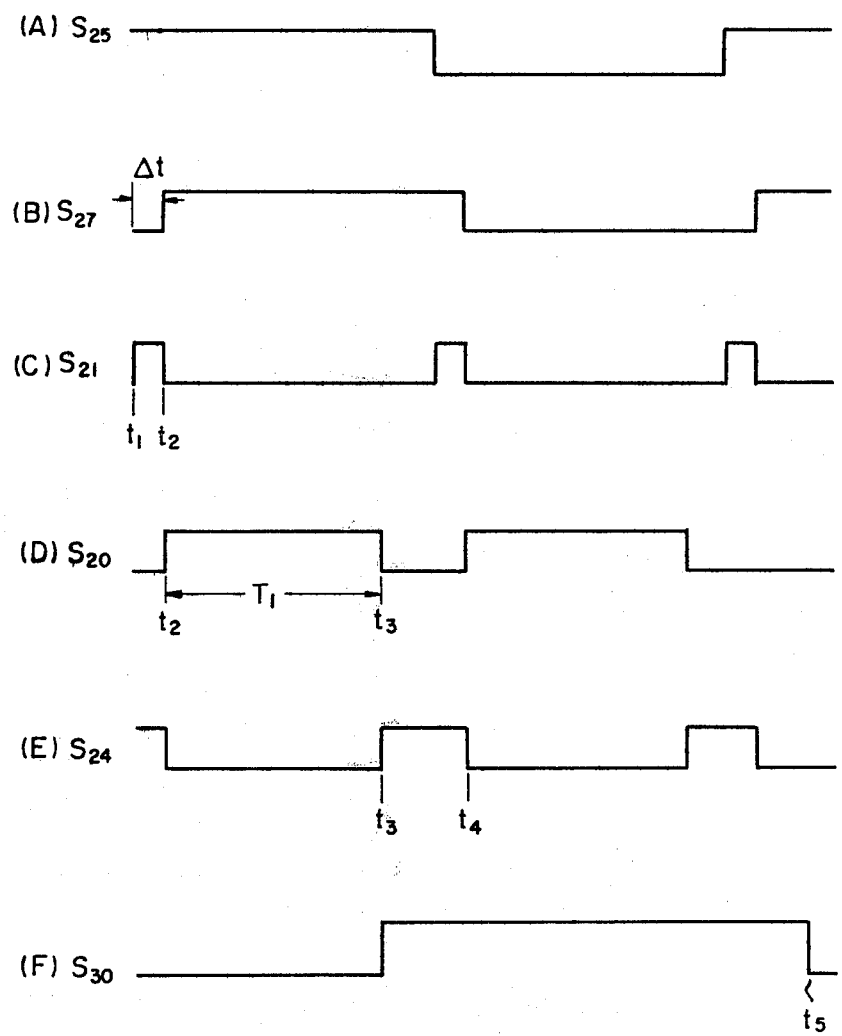
Figure 12A:
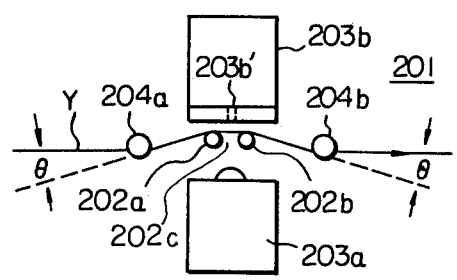
FIG. 12A is a schematic side view of essential elements of a portable type apparatus according to the present invention.

The control circuit 112 comprises a clock pulse generator 126 which generates a clock pulse signal $S_{25}$ with a predetermined frequency as shown in FIG. 11A. The signal $S_{25}$ is applied to one input terminal of an exclusive-OR gate 128, and also is applied to the other input terminal of the exclusive-OR gate 128 through a delay circuit 129 which delays the signal by a time of $\Delta t$. Therefore, the timing signal $S_{21}$, as shown in FIG. 11C, can be obtained from the out put of the exclusive-OR gate 128. As described above, the timing pulse signal $S_{21}$ is applied to the counter 117 as reset pulses, and moreover, is applied to the switchover circuit 111 and the selectors 120, 122.

In order to produce the gate signal $S_{20}$, the control circuit 112 also comprises a timer 130 to which the timing pulse signal $S_{21}$ is supplied as a reset signal. The timer 130 produces the gate signal $S_{20}$, the level of which becomes high for a predetermined time $T_1$ set by the timer after the timer 130 is reset. In the present embodiment, the above-mentioned time set by the timer 130 is adjusted to a time necessary for the yarn $Y_O$ to run along 10 m. Since the timer 130 is reset at the time of falling of the timing pulse signal $S_{21}$, the level of the gate signal $S_{20}$ becomes high at the time $t_2$, and become low at the time $t_3$ when the time $T_1$ has lapsed after the reset operation as shown in FIG. 11D. Therefore, the AND gate 116 is open for the time $T_1$. The signal $S_{20}$ is inverted by using an inverter 131, and this inverted signal is applied to the AND gates 121 and 123 as the gate signal $S_{24}$ shown in FIG. 11E.

The operation of the integrated inspection panel 100 will be explained in conjunction with FIGS. 9, 9B, 10 and 11. At first, prior to the measuring operation, the R-S flip-flops 134a to 134n and 135a to 135n are reset by closing the switch 132. When the level of the timing pulse signal $S_{21}$ becomes high at the time $t_1$, the switchover circuit 111 and the selectors 120 and 122 are switched over to select one of the interlacing degree detector and lamps corresponding to the selected spindle. At the same time, the counter 117 is reset. After this, the timer 130 is started by the falling of the timing pulse signal $S_{21}$ at the time of $t_2$, and as a result, the level of the gate signal $S_{20}$ becomes high at the time $t_2$ to open the AND gate 116. When the level of the gate signal $S_{20}$ becomes low at the time of $t_3$, the AND gate 116 is closed. Consequently, the counter 117 counts the number of the pulses which are applied to the counter 117 during the time from $t_2$ to $t_3$, and the compared results in the detecting circuits 118 and 119 are applied to the AND gates 121 and 123. Since the gate control signal $S_{24}$ is applied to the AND gates 121 and 123, each of the compared results is supplied to each selector, during the time from $t_3$ to $t_4$, respectively. In this embodiment, the time interval $T_1$ between $t_2$ and $t_3$ is adjusted to a time necessary for the yarn $Y_O$ to run along 10 [m]. Therefore, the value $V_{UL}$ is set at the maximum number of the interlaced portions per 10[m] and the value $V_{LL}$ is set at the minimum number of the interlaced portion per 10[m] of the yarn $Y_O$.

Consequently, if the input value from the counter 117 is larger than the upper limit value $V_{UL}$, the R-S flip-flop selected by the selector 120 is set at the time of $t_3$, and the lamp connected to the selected R-S flip-flop is lit. As a result, the alarm display operation is carried out. This alarm display operation is continued until the push-button switch 132 is pressed to reset the R-S flip-flop at the time $t_5$. As described above, since the alarm display operation can be continued until the completion of the operators inspection whether there are any abnormal spindle units or not. It is possible to surely sense the occurrence of the abnormal condition in the spindles. On the other hand, if the input value from the counter 177 is smaller than the lower limit value $V_{LL}$, since the R-S flip-flop selected by the selector 122 is set at the time $t_3$, and the lamp connected to the selected R-S flip-flop is lit, Therefore, in this case, the alarm display operation can be carried out.

When the level of the timing pulse signal $S_{21}$ becomes high again at the time $t_4$, the switchover circuit 111 is switched over so as to select the signal from the interlacing degree detector at the next spindle, and, at the same time, each of the selectors 120 and 122 is actuated so as to select each lamp corresponding to the selected spindle in syncronization with the operation of the switchover circuit 111. After this, the interlacing degree computing circuit 113 operates in the same manner as described above.

In the above described manner, the yarns $Y_O$ in the spindles can be automatically inspected by the panel 100 in sequence.

The foregoing embodiment of the integrated inspection according to the scanner system utilizing the switchover circuit has been found to be effective for simplification of the circuit structure. However, from the viewpoint of gurantee of the quality, completely continuous inspection is preferred. In this case, the above-mentioned circuit structure must be laid out for each of the interlacing degree detectors 99 of the respective spindle units to effect inspection in a continuous manner in the respective spindle units.

In the above mentioned embodiment, a circuit for counting the number of interlaced portions appearing for a unit time is used as the abnormal condition detecting circuit 113. Since the manufacturing conditions are uniform in the actual manufacturing equipment, there can be attained effects due to simplifying the structure of the apparatus and stabilizing the scanning period by adoption of this circuit arrangement.

The circuit structue is not limited to the one specifically illustrated in the above mentioned embodiment. The intended objects can be attained so long as a circuit capable of separating an alternating current component from an electric analog signal put out from the light receiving device 102 and counting and displaying peaks of the separated alternating current component is used as the circuit 113. Further, if a yarn cutting device is disposed between the yarn guide 83 and the snap pin 85 so that the cutting device is actuated by the abnormal signal, automatic yarn threading becomes possible.

In the above mentioned embodiment, the apparatus of the present invention is applied to the false twist-drawing machine. Needless to say, the present invention can directly be applied to the interlacing process in which yarns are interlaced and the degree of interlacing should be inspected.

As will be apparent from the above mentioned illustration, on-line inspection of the interlaced yarn manufacturing process, which is impossible according to the conventional technique, can be accomplished effectively according to the present invention and determination of the degree of interlacing at the inspecting step becomes unnecessary. Therefore, the labor necessary for the measurement can be saved. Furthermore, deviations of the degree of interlacing owing to the occurrence of an accident or trouble in the interlaced yarn manufacturing process, can be promptly detected and undesirable creation of interlaced yarn portions having an abnormal degree of interlacing into a product package can be effectively prevented. Accordingly, the yarn quality, e.g., the degree of interlacing can be completely guaranteed. Still further, also yarn breakage can be detected and hence, a yarn breakage detector need not be disposed. Thus, according to the present invention, the interlaced yarn manufacturing process can be remarkably improved.

FIGS. 12A to 15 illustrate a portable type apparatus according to the present invention. When it is intended to build the apparatus of the present invention in an existing interlaced yarn manufacturing equipment for the purpose of the process control, a part of the equipment should be reconstructed or remodelled. In the present embodiment, there is provided a portable type apparatus for determining the degree of interlacing, which is suitable for measuring the degree of interlaced yarns being manufactured in the existing interlacing manufacturing machine. When the portable type apparatus of the present embodiment is employed, expenses necessary for the above-mentioned reconstructions or remodelling can be saved. The structure and effect of the present embodiment will now be described in detail with reference to the accompanying drawings FIGS. 12A to FIG. 15.

As shown in those drawings, an interlacing degree detecting zone 201 comprises:
- a contact body including a pair of yarn contact rods 202a and 202b disposed in parallel to each other;
- a photoelectric detector including a projector 203a and a light receiving device 203b, which are disposed so that the light axis between them extends in the vertical direction of a gap 202c between the yarn contact rods 202a and 202b, to detect changes of the configuration of a yarn $Y_O$ and;
- yarn guides 204a and 204b disposed on both sides of the yarn contact rods 202a and 202b along the threadline direction of the yarn $Y_O$, which is caused to run while being bent by the yarn guides 204a and 204b and the above-mentioned yarn contact rods 202a and 202b.

In order to enhance the sensitivity of detection of the change of the configuration of the yarn $Y_O$, a slit 203b' is formed on the front face of the light receiving device 203b. Yarn grooves 204a' and 204b' are formed on the yarn guides 204a and 204b so that the yarn $Y_O$ can run stably in a direction intersecting the above-mentioned light axis. When the yarn is caused to run while being bent as shown in the drawing (FIG. 12A), a compressive contact force is produced by the tension of the yarn $Y_O$ and the yarn $Y_O$ is pressed on the yarn contact rods 202a and 202b.

Figure 15:
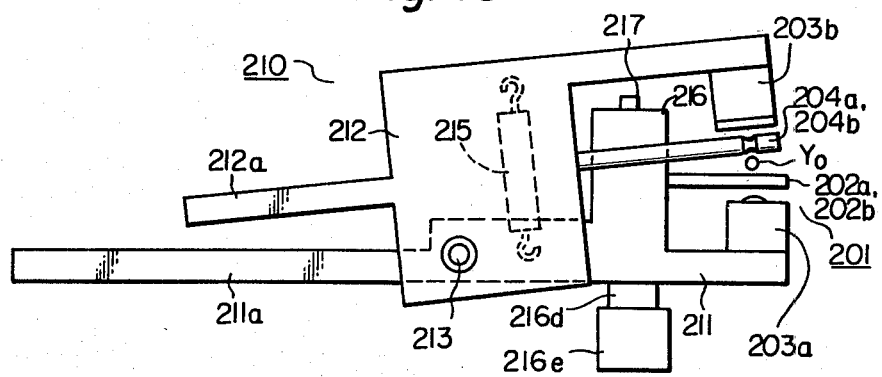
FIG. 15 is a schematic side view, in the opened condition, of the apparatus illustrated in FIG. 13A.
Figure 13A:
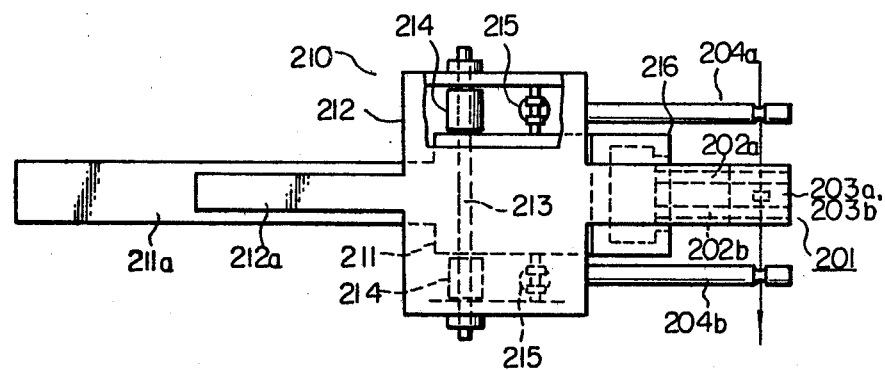
FIG. 13A is a schematic plan view of the practical portable apparatus according to the present invention.
Figure 13B:
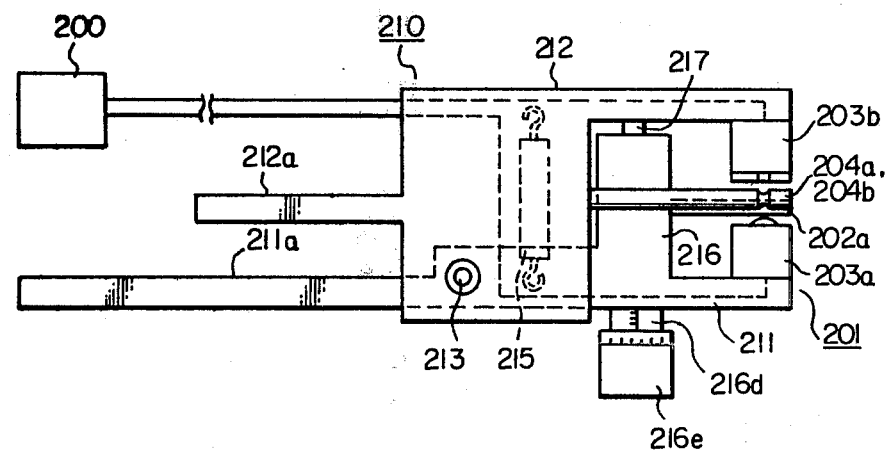
FIG. 13B is a schematic side view of the apparatus illustrated in FIG. 13A.

The interlacing degree measuring head 210 of the present embodiment has a structure as shown in FIGS. 13A, 13B and 15. First and second supporting members 211 and 212, the rear ends of which are formed into hold portions 211a and 212a, respectively, are connected to each other in the intermediate portions through a shaft 213 so that the top end portions of the supporting members 211 and 212 are opened when the hold portions 211a and 212a are held. The yarn contact rods 202a and 202b and projector 203a are attached to the first supporting member 211 and the yarn guides 204a and 204b and light receiving device 203b are attached to the second supporting member 212, so that they are located on the insides of the confronting surfaces of the top end portions of both the supporting members 211 and 212. Both the supporting members 211 and 212 are arranged so that when they are present at the measurement positions, namely in the closed state as shown in the drawings FIGS. 13A and 13B, the above-mentioned interlacing degree detecting zone 201 is constructed in the top end portions of the supporting members 211 and 212. A distance piece 214 is disposed to prevent deviations of the positions of the first and second supporting members 211 and 212 in the direction of the shaft 213. A restoring spring 215 is disposed to return the first and second supporting members 211 and 212 to the measurement positions. An attachment member 216 is disposed to attach the contact rods 202a and 202b to the first supporting member 211 movably in a direction intersecting the passage of the yarn $Y_O$ at a right angle, namely in the vertical direction in the drawing (FIG. 13B). A stopper 217 is disposed on the top end of the attachment member 216 to define the gap between both the supporting members 211 and 212 at the above-mentioned measurement positions.

Figure 14A:
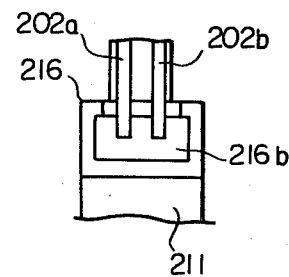
FIG. 14A is a schematic plan view of the yarn guide device utilized for the apparatus illustrated in FIG. 13A.
Figure 12B:
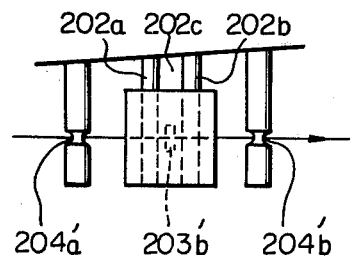
FIG. 12B is a schematic plan view of the apparatus illustrated in FIG. 12A.
Figure 14B:
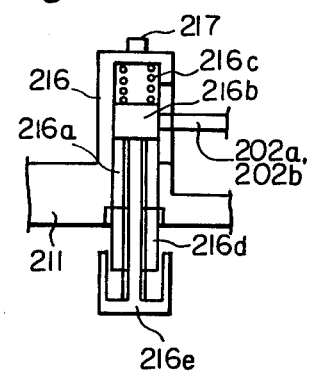
FIG. 14B is a schematic side view of a part of the apparatus illustrated in FIG. 13A.

Attachment of the yarn contact rods 202a and 202b to the attachment member 216 is accomplished in a manner as shown in FIGS. 14A and 14B. A through hole 216a piercing from the first supporting member 211 to the interior of the attachement member 216 is formed, and a sliding block 216b is slidably disposed in the through hole 216a by means of a spring 216c and an adjustment rod 216e screwed to an attachment piece 216d fitted to the first supporting member 211, and the yarn contact rods 202a and 202b are fixed to this sliding block 216b. Needless to say, the attachment member 216 is opened on the side to which the yarn contact rods 202a and 202b are attached, so that the contact rods 202a can move in the vertical direction in the drawing (FIG. 14B). The attachment piece 216d and the hold portion of the adjustment rod 216e are graduated as shown in FIG. 13B, so that positions of the yarn contact rods can be precisely set.

In the interlacing degree measuring head 210 of the present embodiment, when the hold portions 211a and 212a of both the supporting members 211 and 212 are held, the top end portions thereof are opened as shown in FIG. 15. Accordingly, the yarn $Y_O$ can easily be threaded to the measurement head 210 even during the manufacture. Further, since the yarn contact rods 202a and 202b are arranged so that they can move, the inclination angle $\theta$ (FIG. 12A) of the yarn $Y_O$ can be appropriately adjusted. Therefore, even if the tension of the yarn $Y_O$ is fixed as in the case where the yarn $Y_O$ is being manufactured, the compressive contact force F can be adjusted to a desirable level according to the above-mentioned formula. As will be apparent to those skilled in the art, the inclination angle $\theta$ can also be adjusted by arranging the yarn guides 204a and 204b so that their positions can be shifted.

Figure 16:
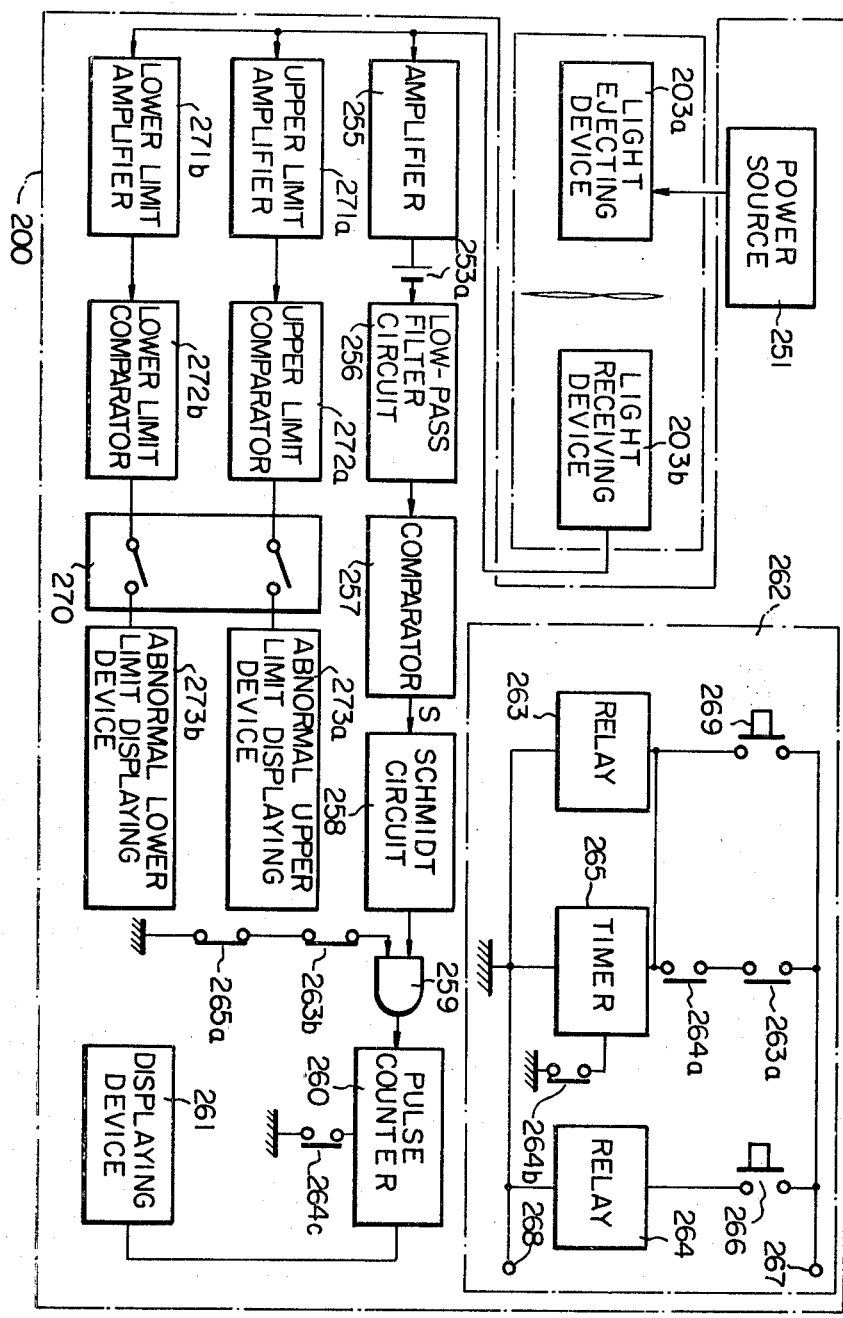
FIG. 16 is a block diagram of the measurement circuit utilized for the portable apparatus illustrated in FIG. 13A.

The structure of a measurement circuit 200 and the method for determining the degree of interlacing in a yarn $Y_O$, being manufactured, by means of the above-mentioned measurement head 210 and the measurement circuit 200 will now be described with reference to FIG. 16.

The tension and running speed of the yarn $Y_O$ are measured or calculated from the manufacturing conditions. The measuring timer according to the running speed is set at a timer 265 (will be described later) mounted on the body portion of the measurement device (not shown), and the tension is set by adjusting the adjustment rod 216e. Then, hold portions 211a and 212a are held to open the interlacing degree detecting zone 201 of the measurement head 210, and the yarn $Y_O$ is then threaded and the hold portion 212a is separated. At this point, the interlacing degree detecting zone 201 is restored to the measurement position and changes of the configuration of the yarn $Y_O$ are caused on the yarn contact rods 202a and 202b and in the gap therebetween according to the state of interlacing. Thus, the measurement becomes possible in this state. The construction and operation of the measurement circuit 200 will now be described.

The quantity of light transmitted to the light receiving device 203b from the projector 203a actuated by a power source 251 of the measurement circuit 200 is changed according to the above-mentioned change of the configuration of the yarn $Y_O$. As will be apparent from the foregoing illustration, the quantity of light transmitted to the light receiving device 203b is increased when the interlaced portion of the yarn $Y_O$ passes, but the quantity of the light is decreased when the noninterlaced portion of the yarn $Y_O$ passes. The light receiving device 203b detects the change of the quantity of light proportional to the change of the configuration of the yarn $Y_O$ and converts it to an electric analog signal (comprising a direct current component and an alternating current component), and this analog signal is transmitted to an amplifier 255, where the signal is amplified. The direct current component is cut off by a condenser 253a, and the resulting alternating current signal is transmitted to an low-pass filter circuit 256 where a high frequency wave component including in the alternating current signal is cut off by the low-pass filter circuit 256. Then, only an alternating signal exceeding a predetermined level (namely, a signal generated on passage of the interlaced portion) is converted to a pulse signal S by a comparator 257. The pulse signal S is put into a Schmidt circuit 258 where the wave form is shaped. Then, the pulse signal is transmitted to a gate circuit 259. Since the gate circuit 259 is opened by depression of the start button 269 as described hereinafter, the pulse signal S is transmitted to a pulse counter 260 through the AND gate 259 and pulses are counted by the pulse counter 260. The counted output signal from the pulse counter 260 is applied to a displaying device 261 for displaying the number of the interlaced portion of the yarn $Y_O$.

To control opening or closing of the AND gate 259, a control circuit 262 is arranged in the measurement circuit 200. The control circuit 262 comprises a relay 263, a relay 264, and a timer 265. The relay 264 is connected to a push-button switch 266 for reset in series and the series circuit of the relay 264 and the push-button switch 266 is connected between terminals 267 and 268 to which a power source (not shown) is connected. Therefore, when the push-button switch 266 is pushed the relay 264 is energized to open a switch 264a. The relay 263 is connected between the terminals 267 and 268 through a push-button switch 269, and the series circuit of the switch 264a and a switch 263a, which is closed when the relay 263 is energized, is connected to the switch 269 in parallel. The timer 265 is connected to the relay 263 in parallel. The other input terminal of the AND gate 259 is grounded through a normally closed switch 263b actuated by the relay 263 and a normally closed switch 265a actuated by the timer 265. In addition, the timer 265 and the pulse counter 260 are adapted to be reset by closing switches 264b and 264c, respectively. The switches 264b and 264c are closed at the same time only when the relay 264 is energized. Opening or closing of the AND gate 259 is controlled in the following manner.

At first, when the switch 266 is depressed, the switches 264b and 264c are closed and the timer 265 and the pulse counter 260 are reset. When the switch 269 is depressed after opening the switch 266, the relay 263 is energized to close the switch 263a. Therefore, the relay 263 is kept in the energized condition, and, at the same time, the operation of the timer 265 is started to open the switch 265a. As a result, since the switch 265a is open, the AND gate 259 permits the pulses from the Schmidt circuit 258 to pass through and, after a predetermined time which is set by the timer 265, the switch 265a is closed so that the AND gate 259 is closed. Namely, when the push-button switch 269 is depressed, at the same time the operation of a timer 265 is started to open the AND gate 259, and after the lapse of the time set in the timer 264, the AND gate 259 is closed.

Accordingly, if the time set in the timer 264 is set at the time necessary for the yarn $Y_O$ to run 10 meters along the path, the number of interlaced portions per 10 meters of the yarn length is displayed on the displaying device 261. Since the figure on the displaying device 261 is shifted upward by one place, the displayed value directly indicates the number of interlaced portions per meter of the yarn length, i.e., the degree of interlacing. When the push-button switch 266 for reset is depressed and then the push-button switch 269 is depressed, the measurement is started again in the same manner described hereinbefore. In addition, it is very convenient for the measuring operation to calibrate the scale of the timer 265 in terms of the yarn speed readings, if the measuring operation is carried out for the yarn $Y_O$ of length of 10 meters.

A circuit for detecting a trouble or accident in the projector 203a and the light receiving device 203b is attached to the above-mentioned measurement circuit 200. This circuit is used before initiation of the measurement. Before the initiation of the measurement, since the yarn $Y_O$ is not present, the quantity of light transmitted to the light receiving device 203b from the projector 203a is constant and a direct current signal is put out from the light receiving device 203b. This direct current signal is amplified by an upper limit amplifier 271a and a lower limit amplifier 271b, and the amplified signal is compared with prescribed upper limit and lower limit values by upper limit and lower limit comparators 272a and 272b. When a check switch 270 is closed, if trouble or an accident takes place, specifically if the compared signal is larger than the prescribed upper limit value or smaller than the prescribed lower limit value, an abnormal upper limit displaying device 273a or abnormal lower limit displaying device 273b is lit to indicate occurrence of trouble or an accident. This circuit for detecting trouble or an accident is very effective when an alternating current analog signal is obtained by photoelectric conversion and valuable information is extracted from the level of this analog signal as in the present embodiment.

What is claimed is:

1. A method for determining the state of interlacing in interlaced multifilament yarns, which comprises causing an interlaced multifilament yarn to run while being in contact with a contact member under a predetermined contact pressure, thereby to produce temporary changes of the configuration in the yarn according to the state and structure of the yarn, detecting the changes of the configuration in the form of time series values and processing the detected values to determine interlacing characteristics of the yarn.

2. A method for determining the state of interlacing in interlaced multifilament yarns according to claim 1, wherein the interlaced condition in the yarn is determined from changes of the predetermined contact pressure.

3. A method for determining the state of interlacing in interlaced multifilament yarns according to claim 1 wherein the change of the configuration is photoelectrically detected in the form of an electric analog signal comprising a direct current component and an alternating current component, the electric analog signal is electrically processed to extract a time series alternating current component alone, said alternating current component is electrically converted to a corresponding time series pulse signal, and the number of pulses is counted and integrated for a predetermined time to obtain a variable indicating the degree of interlacing in the interlaced multifilament yarn.

4. A method for determining the state of interlacing in interlaced multifilament yarns according to claim 3 wherein the length of the interlaced multifilament yarn running for said predetermined time while in contact with the contact member is measured and the number of the integrated pulses is divided by the measured value of the yarn length to determine the degree of interlacing in the interlaced multifilament yarn.

5. A method for determining the state of interlacing in interlaced multifilament yarns according to claim 3 wherein the degree of interlacing in the interlaced yarn is measured in an interlaced yarn take-up passage of an interlaced yarn manufacturing process and the measurement of the degree of interlacing is carried out intermittently on the same interlaced yarn to determine the total quantity of the degree of interlacing in the interlaced yarn.

6. A method for determining the degree of interlacing in interlaced multifilament yarns according to claim 1 wherein the change of the configuration of the interlaced multifilament yarn is detected in the form of an electric analog signal comprising a direct current component and an alternating current component, said electric analog signal is electrically processed to extract a time series alternating current component alone, said extracted alternating current component is electrically converted to a time series pulse signal, the time between two adjacent pulses is electrically detected from generation points of the two pulses of said pulse signal, and an alarm is given when said electrically detected value exceeds an upper limit of a predetermined allowable range or is below a lower limit of said predetermined allowable range.

7. A method for determining the state of interlacing in interlaced multifilament yarns according to claim 6 wherein the measurement of the degree of interlacing in the interlaced yarn is carried out in an interlaced yarn take-up passage of an interlaced yarn manufacturing process.

8. A method for determining the state of interlacing in interlaced multifilament yarns according to claim 1 wherein the state of interlacing is detected in an interlaced yarn take-up passage with respect to each spindle of an interlaced yarn manufacturing process including a plurality of processing spindles and the detected states in the respective spindles are integrally inspected.

9. A method for determining the degree of interlacing an interlaced multifilament yarns according to claim 1 wherein the state of interlacing is detected in an interlaced yarn take-up passage with respect to each spindle of an interlaced yarn manufacturing process including a plurality of processing spindles and the detected states in the respective spindles are displayed in sequence.

10. A method for determining the degree of interlacing in interlaced multifilament yarns according to claim 1 wherein said predetermined contact pressure is 2 to 20 g of the interlaced multifilament yarn.

11. An apparatus for determining the state of interlacing in interlaced multifilament yarns, which comprises a detecting element including guide means for guiding an interlaced multifilament yarn along a predetermined yarn passage, at least one contact member having contact with the yarn passing through said yarn passage under a predetermined contact pressure, and a light source and a light receiving device, which are arranged so that the light axis between them intersects the yarn passage in the vicinity of a contact point where the yarn first falls into contact with said contact member.

12. An apparatus according to claim 11 which further comprises electric means for extracting a time series alternating current component alone from a signal emitted from said light receiving device and converting it to a corresponding time series pulse signal and another electric means for processing said pulse signal to produce and emit a signal indicating the state of interlacing.

13. An apparatus according to claim 11 which further comprises measuring means for measuring the length of the yarn running during the period of the detection of the state of interlacing while being in contact with the contact member and computing means for automatically computing the degree of interlacing indicating the state of interlacing from the signal of the electric means indicating the state of interlacing and the measurement signal of said measuring means.

14. An apparatus according to claim 11 wherein said detecting element is disposed on the downstream side of an interlaced yarn take-up passage of each interlacing spindle of an interlaced yarn manufacturing machine.

15. An apparatus according to claim 14 further comprising integrated inspection means for displaying signals from the light receiving devices of the detecting elements of the respective spindles.

16. An apparatus according to claim 15 wherein said integrated inspection means comprises means for electrically processing the signals from the light receiving devices of the detecting elements of the respective spindles and changeover means for changing over in sequence connections of said electric means emitting a signal indicating the state of interlacing to the light receiving devices of the detecting elements of the respective spindles.

17. An apparatus according to claim 12 wherein said electric means for emitting a signal indicating the state of interlacing in the interlaced multifilament yarn is an electric means for generating a time series electric signal of an intensity corresponding to the time between the points of generation of adjacent pulses of the time series pulse signal emitted from said time series pulse signal-emitting electric means and electric discriminating means is disposed to produce a particular electric signal when said time series electric signal is below or above a predetermined allowable lower or upper limit.

18. An apparatus according to claim 17 which further comprises an alarm device to be actuated by said particular electric signal produced by said electric discriminating means.

19. An apparatus according to claim 12 further comprising a measurement head, said measurement head comprising a pair of supporting members connected to each other at intermediate portions, the rear end portions of said supporting members are formed into hold portions and the top end portions of the supporting members are arranged so that they can be opened and closed, and the guide means of said detecting element and one of the light source and light receiving device are attached to one of said supporting members and the other of the light source and light receiving device is attached to the other supporting member so that the light source confronts the light receiving device in the top end portions of the supporting members, whereby the detecting element is placed in the operational state when said supporting members are closed.

20. An apparatus according to claim 11 wherein the contact member has a convex contact surface in the yarn contact portion.

21. An apparatus according to claim 20 wherein at least the yarn contact portion of the yarn contact member is made of a light-transmitting material.

22. An apparatus according to claim 20 wherein the contact member is constructed in such a way that the yarn comes into contact with the contact member at two points which are along the yarn path and are separated from each other by a predetermined distance.

23. An apparatus according to claim 11 wherein said contact member, light source and light receiving device are attached to one bracket.

24. An apparatus according to claim 11 further comprising a slit suitable for a thickness of the yarn which is disposed at said light axis for restricting the amount of the transmitting light from said light source to said light receiving device.

* * * * *

UNITED STATES PATENT OFFICE
CERTIFICATE OF CORRECTION

Patent No. 4,213,056  Dated July 15, 1980

Inventor(s) Seiji Matsumura, et al

It is certified that error appears in the above-identified patent and that said Letters Patent are hereby corrected as shown below:

Column 16, line 61: "lever" should be --level--.

Column 18, line 11: "manifacturing" should be --manufacturing--.

Column 20, line 57: After "lit" change the comma to a period.

Column 21, line 8: "gurantee" should be --guarantee--.

line 22: "structue" should be --structure--.

Column 24, line 27: "displying" should be --displaying--.

Column 25, line 19: "8" should be --a--; after "or" insert --an--.

Signed and Sealed this

Thirtieth Day of December 1980

[SEAL]

Attest:

SIDNEY A. DIAMOND

Attesting Officer

Commissioner of Patents and Trademarks